United States Patent [19]

Henner et al.

[11] Patent Number: 5,464,756

[45] Date of Patent: Nov. 7, 1995

[54] PROCESSES AND COMPOSITIONS FOR THE ISOLATION OF HUMAN RELAXIN

[75] Inventors: Dennis J. Henner, Pacifica; Richard L. Vandlen, Hillsborough; James A. Wilkins, San Mateo; Daniel G. Yansura, Pacifica, all of Calif.

[73] Assignee: Genentech, San Francisco, Calif.

[21] Appl. No.: 908,766

[22] Filed: Jul. 1, 1992

Related U.S. Application Data

[63] Continuation of Ser. No. 347,550, May 4, 1989, abandoned.

[51] Int. Cl.[6] .............................. C12P 21/06; C12P 21/02; C12N 15/70; C12N 15/12
[52] U.S. Cl. .................... 435/69.1; 435/69.2; 435/69.7; 435/70.1; 435/70.3; 435/252.33; 435/849; 530/344; 530/345; 530/350; 530/427; 530/300; 930/240; 930/310; 930/DIG. 534; 935/73
[58] Field of Search .............................. 435/69.6, 172.3, 435/320.1, 69.1; 530/345; 935/47

[56] References Cited

U.S. PATENT DOCUMENTS

| | | | |
|---|---|---|---|
| 4,758,516 | 7/1988 | Hudson et al. | 435/252.3 |
| 4,835,251 | 5/1989 | Burnier et al. | 530/324 |
| 4,871,670 | 10/1989 | Hudson et al. | 435/172.3 |

FOREIGN PATENT DOCUMENTS

| | | |
|---|---|---|
| 0055945 | 7/1982 | European Pat. Off. |
| 0068375 | 1/1983 | European Pat. Off. |
| 0195691 | 9/1986 | European Pat. Off. |
| 0281418 | 9/1988 | European Pat. Off. |
| 0287820 | 10/1988 | European Pat. Off. |
| 0303033 | 2/1989 | European Pat. Off. |

OTHER PUBLICATIONS

Inglis, 1983, Methods in Enzymology 91:324–332.
Landon et al. Meth. Enzymol. 1977 (47):145.
Nishikawa et al. 1987 Protein Eng 1(6):487, Abstract.

*Primary Examiner*—Jasemine C. Chambers
*Assistant Examiner*—Brian R. Stanton
*Attorney, Agent, or Firm*—Pennie & Edmonds

[57] ABSTRACT

A process is provided for cleaving a polypeptide into at least two polypeptide components comprising treating a reduced, free-cysteine form of the polypeptide with a cleaving agent under conditions for cleaving the polypeptide at a desired junction between the polypeptide cleavage products. More preferably, the process for cleaving comprises culturing cells containing DNA encoding said polypeptide, wherein at least one Asp codon is present in said DNA at a desired junction between the components to be cleaved from each other, said culturing resulting in expression of the DNA to produce the polypeptide in the host cell culture; and treating a reduced, free-cysteine form of the polypeptide with dilute acid under conditions for cleaving the polypeptide at the Asp junction. In particular embodiments, a DNA sequence is provided that encodes a relaxin precursor and includes codons encoding aspartic acid-containing linkers at novel positions within the precursor, allowing the ready cleavage of relaxin A peptides by treatment with dilute acid.

15 Claims, 17 Drawing Sheets

| | 1 | | | 5 | | | | 10 | | | | 15 | | | | 20 | | | | 24 |
|---|---|---|---|---|---|---|---|---|---|---|---|---|---|---|---|---|---|---|---|---|
| R.MONKEY | GLN | LEU | TYR | MET | THR | LEU | SER | ASN | LYS | CYS | CYS | HIS | ILE | GLY | CYS | THR | LYS | LYS | SER | LEU | ALA | LYS | PHE | CYS |
| HUMAN-2 | GLN | LEU | TYR | SER | ALA | LEU | ALA | ASN | LYS | CYS | CYS | HIS | VAL | GLY | CYS | THR | LYS | ARG | SER | LEU | ALA | ARG | PHE | CYS |
| HUMAN-1 | ARG | PRO | TYR | VAL | ALA | LEU | PHE | GLU | LYS | CYS | CYS | LEU | ILE | GLY | CYS | THR | LYS | ARG | SER | LEU | ALA | LYS | TYR | CYS |
| PIG | | ARG | MET | THR | LEU | SER | GLU | LYS | CYS | CYS | GLN | VAL | GLY | CYS | ILE | ARG | LYS | ASP | ILE | ALA | ARG | LEU | CYS |
| RAT | GLN | SER | GLY | ALA | LEU | LEU | SER | GLY | GLN | CYS | CYS | HIS | ILE | GLY | CYS | THR | ARG | ARG | SER | ILE | ALA | LYS | LEU | CYS |
| MOUSE | GLU | SER | GLY | GLY | LEU | MET | SER | GLN | GLN | CYS | CYS | HIS | VAL | GLY | CYS | SER | ARG | ARG | SER | ILE | ALA | LYS | LEU | TYR | CYS |
| SHARK-ST | ALA | THR | SER | PRO | ALA | MET | SER | ILE | LYS | CYS | CYS | ILE | TYR | GLY | CYS | THR | LYS | LYS | ASP | ILE | SER | VAL | LEU | CYS |
| SHARK-D | GLU | GLY | SER | PRO | GLY | MET | SER | SER | LYS | CYS | CYS | THR | TYR | GLY | CYS | THR | ARG | LYS | ASP | ILE | SER | ILE | LEU | CYS |

Fig. 1.A

| | 1 | | | | 5 | | | | | 10 | | | | 15 | | | | | 20 | | | | 24 |
|---|---|---|---|---|---|---|---|---|---|---|---|---|---|---|---|---|---|---|---|---|---|---|---|
| R.MONKEY | GLN | LEU | TYR | MET | THR | LEU | SER | ASN | LYS | CYS | CYS | HIS | ILE | GLY | CYS | THR | LYS | SER | LEU | ALA | LYS | PHE | CYS |
| HUMAN-2 | GLN | LEU | TYR | SER | ALA | LEU | ALA | ASN | LYS | CYS | CYS | HIS | VAL | GLY | CYS | THR | LYS | ARG | SER | LEU | ARG | PHE | CYS |
| HUMAN-1 | ARG | PRO | TYR | VAL | ALA | LEU | PHE | GLU | LYS | CYS | CYS | LEU | ILE | GLY | CYS | THR | LYS | ARG | SER | LEU | ALA | LYS | CYS |
| PIG | | | ARG | MET | THR | LEU | SER | GLU | LYS | CYS | CYS | GLN | VAL | GLY | CYS | ILE | ARG | LYS | ASP | ILE | ALA | ARG | CYS |
| RAT | GLN | SER | GLY | ALA | LEU | LEU | SER | GLY | LEU | CYS | CYS | HIS | ILE | GLY | CYS | THR | ARG | ARG | SER | ILE | ALA | LYS | LEU | CYS |
| MOUSE | GLU | SER | GLY | LEU | GLY | MET | SER | GLN | GLN | CYS | CYS | HIS | VAL | GLY | CYS | SER | ARG | ARG | SER | ILE | ALA | LYS | LEU | CYS |
| SHARK-ST | ALA | THR | SER | PRO | ALA | MET | SER | ILE | LYS | CYS | CYS | ILE | TYR | GLY | CYS | THR | LYS | ASP | ILE | SER | VAL | LEU | CYS |
| SHARK-D | GLU | GLY | SER | PRO | GLY | MET | SER | SER | LYS | CYS | CYS | THR | TYR | GLY | CYS | THR | ARG | LYS | ASP | ILE | SER | ILE | LEU | CYS |

| FIG. 1A |
|---|
| FIG. 1B |

Fig. 1B

|        |     |     |     | 1   |     |     |     | 5   |     |     |     |     | 10  |     |     |     |     | 15  |     |     |     |
|--------|-----|-----|-----|-----|-----|-----|-----|-----|-----|-----|-----|-----|-----|-----|-----|-----|-----|-----|-----|-----|-----|
| R.MONKEY |   |   |   | LYS | TRP | MET | ASP | ASP | VAL | ILE | LYS | ALA | CYS | GLY | ARG | GLU | LEU | VAL | ARG | ALA | GLN |
| HUMAN-2 |   |   | ASP | SER | TRP | MET | GLU | GLU | VAL | ILE | LYS | LEU | CYS | GLY | ARG | GLU | LEU | VAL | ARG | ALA | GLN |
| HUMAN-1 |   |   |   | LYS | TRP | LYS | ASP | ASP | VAL | ILE | LYS | LEU | CYS | GLY | ARG | GLU | LEU | VAL | ARG | ALA | GLN |
| PIG |   |   |   | GLN | SER | THR | ASN | ASP | PHE | ILE | LYS | ALA | CYS | GLY | ARG | GLU | LEU | VAL | ARG | LEU | TRP |
| RAT | ARG | VAL | SER | GLU | GLU | TRP | MET | ASP | VAL | ILE | GLN | VAL | CYS | GLY | ARG | GLY | TYR | ALA | ARG | ALA | TRP |
| MOUSE | ARG | VAL | SER | GLU | GLU | TRP | MET | ASP | PHE | ILE | ARG | MET | CYS | GLY | ARG | GLU | TYR | ALA | ARG | GLU | LEU |
| SHARK-ST |   | GLN | SER | LEU | ASN | ALA | GLY | SER | GLY | ILE | LYS | LEU | CYS | GLY | ARG | GLU | PHE | ILE | ARG | ALA | ILE |
| SHARK-D |   | GLN | SER | PHE | ASN | ALA | GLU | PRO | GLY | ILE | LYS | LEU | CYS | GLY | ARG | GLU | PHE | ILE | ARG | ALA | VAL |

|        | 20  |     |     |     |     | 25  |     |     |     |     |     | 29  |     |     | 33  |     |
|--------|-----|-----|-----|-----|-----|-----|-----|-----|-----|-----|-----|-----|-----|-----|-----|-----|
| R.MONKEY | ILE | ALA | ILE | CYS | GLY | LYS | SER | THR | LEU | GLY | LYS | ARG | SER | LEU |   |   |
| HUMAN-2 | ILE | ALA | ILE | CYS | GLY | MET | SER | THR | TRP | SER | LYS | ARG | SER | LEU |   |   |
| HUMAN-1 | ILE | ALA | ILE | CYS | GLY | MET | SER | THR | TRP | SER | LYS | ARG | SER | LEU |   |   |
| PIG | VAL | GLU | ILE | CYS | GLY | SER | VAL | TRP | GLY | ARG | THR | ALA | LEU |   |   |   |
| RAT | ILE | GLU | VAL | CYS | GLY | SER | ALA | SER | TRP | GLY | ARG | ARG | LEU | LEU |   |   |
| MOUSE | ILE | LYS | THR | CYS | GLY | ALA | SER | ALA | SER | VAL | GLY | ARG | LEU | LEU |   |   |
| SHARK-ST | ILE | PHE | ALA | CYS | GLY | GLY | SER | ARG | ARG |   |   |   |   |   |   |   |
| SHARK-D | ILE | TYR | THR | CYS | GLY | GLY | SER | ARG | TRP |   |   |   |   |   |   |   |

Fig. 2A

```
                              haeIII          hinpI
                              xmaIII          hhaI
                              motI thaI       bssHII                           nlaIII  bstNI
                              fnu4HI xmnI     thaI                             fnu4HI bsp1286              ddeI
ATGGACTCTTGATGGAAGAAGTTATCAAACTGTGCGGCCGCGAATTAGTTCGCGCCGCAGATTGCCATTTGCGGCATGAGCACCTGGAGCAAAAGGTCTCTG
TACCTGAGAACCTACCTTCTTCAATAGTTTGACACGCCGGCGCGCTTAATCAAGCGCGGTCTAACGGTAAACGCCTACTCGTGGACCTCGTTTCCAGAGAC
MetAspSerTrpMetGluGluValIleLysLeuCysGlyArgGluLeuValArgAlaGlnIleAlaIleCysGlyMetSerThrTrpSerThrLysArgSerLeu mboII
      scrFI   ddeI
      bstNI sfaNI mnlI                                  fokI
AGCCAGGAAGATGCTCCTCAGACACCTAGACCAGTGGCAGAAATTGTGCCATCCTCATCAACAAAGATACAGAAACCATAAATATGATGTCAGAA
TCGGTCCTTCTACGAGGAGTCTGTGGATCCGTCACCGTCTTTAACAGGTAGTGTTTCTATGTCTTTGGTATTTATACTACAGTCTT
SerGlnGluAspAlaProGlnThrProArgProValAlaGluIleValProSerPheIleAsnLysAspThrGluThrIleAsnMetMetSerGlu fnu4HI
                            alul      hpaI              sfaNI          bbvI                           rsaI
                                     hincII ddeI                                      aluI    nlaIII        hinfI
TTTGTTGCTAATTGCCACAGGAGCTGAAGTTAACCCTGTCTGAGATGCAGCCAGCATTACCACAGCTACAACACAGTGTACCTGTATTAAAAGATTCC
AACAACGATTAAACGGTGTCCTCGACTTCAATTGGGACAGACTCTACGTCGGTCGTAATGGTGTCGATGTTGTGTCATGGACATAATTTCTAAGG
PheValAlaAsnLeuProGlnGluLeuProGlnProAlaLeuProGlnLeuMetSerGluMetGlnProAlaLeuProGlnLeuHisBalProBalLeuLysAspSer mboII
       mboII                                                  fnu4HI                               ddeI
AGTCTTCTCTTTGAAGAATTTAAGAAACTTATTCGCAATAGACAAAGTGAAGCCGCAGACAGCAGTCCTTCAGAATTAAAATACTTAGGCTTGGATACT
TCAGAAGAGAACTTCTTAAATTCTTTGAATAAGCGTTATCTGTTTCACTTCGGCGTCTGTCGTCAGGAAGTCTTAATTTTATGAATCCGAACCTATGA
SerLeuLeuPheGluGluPheLysLysLeuIleArgAsnArgGlnSerGluAlaAlaAspSerSerProSerGluLeuLysTyrLeuGlyLeuAspThr sau3AI
                                                                dpnI
                                                                xhoII
                                   nlaIII  rsaI                 bglII
     taqI
CATTCTCGAAAAAGAGACAACTCTACAGTGCATTGGCTAATAAATGTGCCATGTTGGTTGTACCAAAAGATCTCTTGCTAGATTTTGCTGA
GTAAGAGCTTTTTTCTCTGTTGAGATGTCACGTAACCGATTATTTACACGGTACAACATGTTTCTAGAGAACGATCTAAAACGACT
HisSerArgLysLysArgGlnLeuTyrSerAlaLeuAlaAsnLysCysCysHisValGlyCysThrLysArgSerLeuAlaArgPheCysOP*
```

Fig. 2B

```
                                                                    nlaIII bstNI
                                                              fnu4HI bsp1286           ddeI
ATGGACTCTTGGATGAAGAAGTTATCAAACTGTGCGGCGCCGCGAATTAGTTCGCGCGCAGATTCGCCATTGGGCATGAGCACCTGAGCAAAGGCTCTG
TACCTGAGAACCTACCTTCTTCTTCAATAGTTGACACGCCGCGGCGCGCTTAATCAAGCGCCGTCTAACGGTAAACGCCGTACTCGTGGACCTCGTTTCCAGAGAC
MetAspSerTrpMetGluGluValIleLysLeuCysGlyAlaArgGluLeuValArgAlaGlnIleAlaIleCysGlyMetSerThrTrpSerLysArgSerLeu mboII
    scrFI    ddeI
    bstNI sfaNI mnlI                                       fokI
GATAGCCAGGAAGATGCTCCTCAGACACTGAGCCAGTGCAGAAATTGTGCCATCCTTCATCAACAAAGATACAGAAACCATAAATATGATGTCAGAA
CTATCGGTCCTTCTACGAGGAGTCTGTGGATCTGGTCACCGTCTTTAACACGGTAGAAGTAGTTGTTTCTATGTCTTTGGTATTTATACTACAGTCTT
AspSerGlnGluAspAlaProGlnThrProValAlaGluLeuIleValProSerPheIleAsnLysAspThrGluThrIleAsnMetMetSerGlu fnu4HI
                          hpaI           sfaNI
                 alul    hincII  ddeI bbvI     aluI    nlaIII             rsaI        hinfI
TTTGTTGCTAATTGCCACAGGAGCTGAAGTTAACCCTGTCGAGATGCAGCCAGCATTACCACAGCTACACAACATGTACCTGTATTAAAAGATTCC
AACAACGATTAAACGGTGTCCTCGACTTCAATTGGGACAGACTCTACGTCGGTCGTAATGTGTTGTACATGGTGTACATGACATAATTTCTAAGG
PheValAlaAsnLeuProGlnLeuLysLeuThrLeuSerGluMetGlnProAlaLeuProGlnLeuGlnHisValProValLeuLysAspSer mboII                                                               fnu4HI              ddeI
    mboII
AGTCTTCTCTTTGAAGAATTTAAGAAACTTATTCGCAATAGACAAAAGTGAAGCCGCAGACAGCAGTCCTTCAGAATTAAAATACTTAGGCTTGGATACT
TCAGAAGAGAAACTTCTTAAATTCTTTGAATAAGCGTTATCTGTTTCACTTCGGCGTCTGTCGTCAGGAAGTCTTAATTTTATGAATCCGAACCTATGA
SerLeuLeuPheGluGluPheLysLysLeuIleArgAsnArgGlnSerGluAlaAlaAspSerSerProSerGluLeuLysTyrLeuGluLeuAspThr sau3AI
                                                                               dpnI
                                                                               xhoII
      taqI                                              nlaIII     rsaI     ghlII
CATTCTGAAAAAGAGAGATCAACTCTACAGTGCATTGGCTAATAAATGTTGCCATGTTGGTTGTACCAAAAGATCTCTTGCTAGATTTGCTGA
GTAAGAGCTTTTTCTCTCTAGTTGAGATGTCACGTAACCGATTATTTACAACGGTACAACCAACATGGTTTTCTAGAGAACGATCTAAAACGACT
HisSerArgLysLysArgAspGlnLeuTyrSerAlaLeuAlaAsnLysCysCysHisValGlyCysThrLysArgSerLeuAlaArgPheCysOP*
```

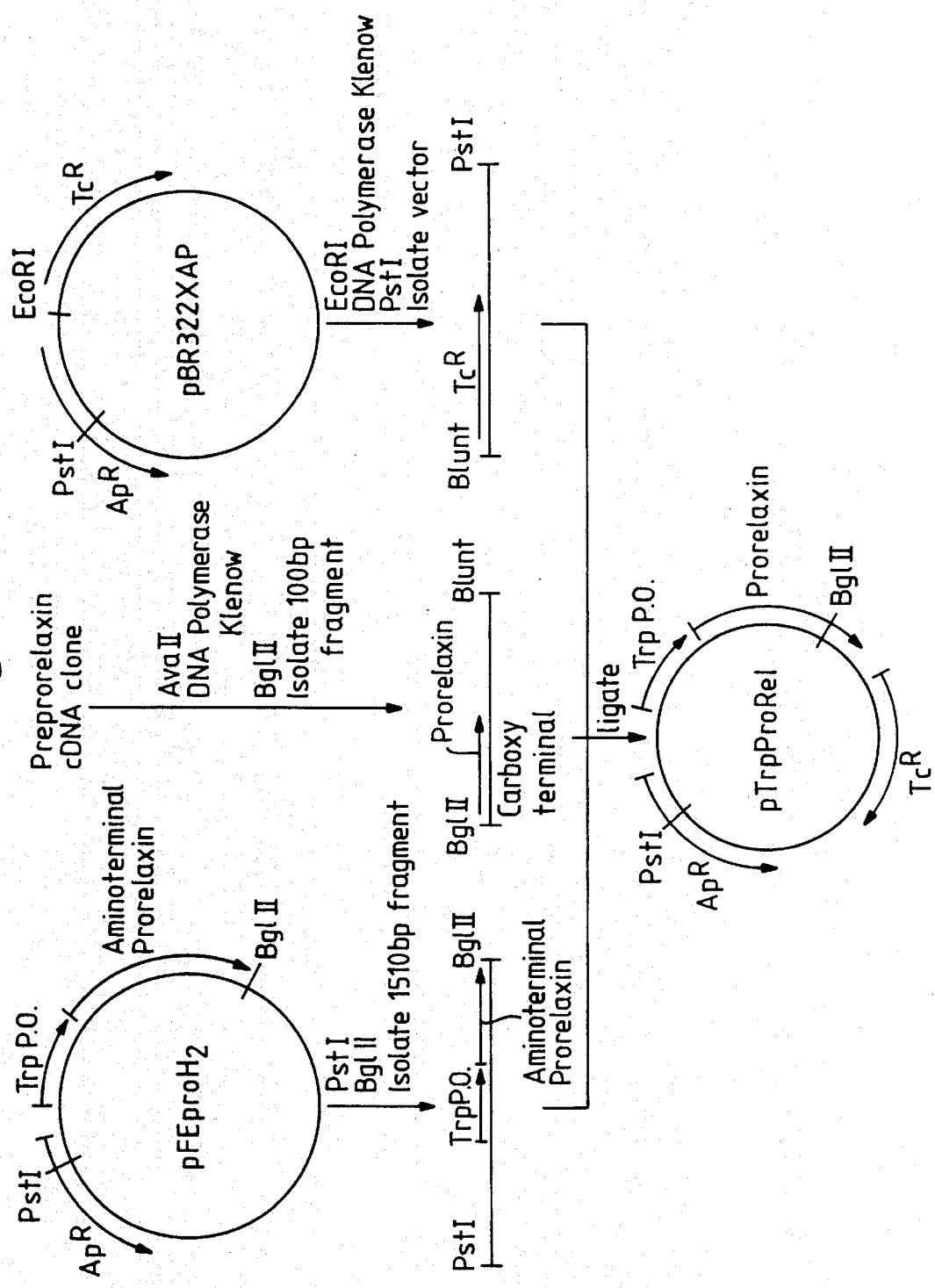

PROCESSES AND COMPOSITIONS FOR THE ISOLATION OF HUMAN RELAXIN

This is a continuation of application Ser. No. 07/347,550, filed on 4 May 1989, now abandoned.

BACKGROUND OF THE INVENTION

1. Field of the Invention

The present invention is directed to improved processes and compositions for the isolation of proteins, and to novel genetic constructions allowing the ready isolation of desired proteins or peptides, particularly multi-chain proteins such as human relaxin that are essentially devoid of aspartic acid ("Asp") residues.

2. Description of Related Disclosures

The production and isolation of desired proteins by recombinant techniques, for example, employing genetically engineered or isolated gene sequences, has in recent years reached a moderate level of sophistication. In fact, it is now possible to produce a variety of proteins by recombinant techniques, including, for example, recombinant human interferon, human growth hormone, or human tissue plasminogen activator, to name just a few, in a variety of hosts, including both eukaryotic and prokaryotic hosts [Maniatis et al., *Molecular Cloning: A Laboratory Manual* (Cold Spring Harbor: New York, 1982)]. Moreover, techniques for moving or "engineering" DNA sequences from one context to another, for example, translocation of sequences from one recombinant vector or host to another vector or host, is currently achievable on a routine basis. Such successes have allowed the production and ready availability of a number of important pharmaceutical and biotechnical products, in a form essentially free of materials normally associated with the protein in its natural environment.

Unfortunately, certain proteins are expressed by recombinant means only with some difficulty. For example, certain proteins, and in particular certain protein hormones, naturally exist in a mature form quite distinct from their cellular nascent form, requiring processing, often the action of a series of enzymes. Such proteins are said to exist in pre-, pro-, or pre/pro-forms. Processing of such proteins will also often result in the generation of two or more individual peptide chains, one or both of which may have biological activity, or which may themselves form bonds or crosslinks resulting in multi-chain proteins, e.g., insulin or relaxin.

The principal problem encountered in generating such proteins is the requirement that pre- and post-sequences, or internally located sequences, be somehow removed to provide the mature protein. Under certain circumstances, such a problem has been reduced or minimized through the use of eukaryotic expression systems wherein the expressed protein or peptide is adequately processed by the eukaryotic host. Unfortunately, such in vivo processing is not always entirely faithful. When this is the case, one is left with a pre- or pro-protein material, often exhibiting only slight or low intrinsic levels of biological activity. Without a convenient means of further processing these proteins, they are only of minimal or no use medically or otherwise. Moreover, in certain instances it is preferable to produce recombinant expression products in a prokaryotic host, such as a bacterium, wherein much larger quantities of expression product may at times be produced more economically.

An example of a protein that ordinarily must be post-translationally modified, e.g., into separate protein chains, is human relaxin. Relaxin is a mammalian peptide hormone that plays an important role in facilitating the birth process through its effects in dilating the pubic symphysis [see, e.g., Hisaw, *Proc. Soc. Exp. Biol. Med.*, 23: 661 (1926)]. Relaxin is synthesized and stored in the corpora lutea of ovaries during pregnancy and is released into the blood stream prior to parturition. Its primary physiological actions appear to be involved in preparing the female reproductive tract for parturition. These actions include dilation and softening of the cervix, inhibition of uterine contractions, and relaxation of the pubic symphysis and other pelvic joints.

The availability of ovaries from pregnant animals has enabled the isolation and amino acid sequence determination of relaxin from pig [see, e.g., Schwabe et al., *Biochem. Biophys. Res. Comm.*, 75: 503–510 (1977); James et al., *Nature*, 267: 544–546 (1977)], rat [John et al., *Endocrinology*, 108: 726–729 (1981)], and even shark [Schwabe et al., *Rec. Progr. Horm. Res.*, 34: 123–211 (1978)]. Moreover, recombinant DNA techniques have allowed the cloning and expression of various relaxins, including, in particular, porcine relaxin [see EPO Pub. No. 86,649] and human relaxin [see, e.g., EPO Pub. No. 101,309 and U.S. Pat. No. 2,758,516, the disclosures of which are incorporated herein by reference].

From the foregoing and other work, it is now known that the relaxin molecule, including both its initial translation transcript (prepro relaxin) and processed mature form (relaxin), bear a striking resemblance to corresponding forms of insulin. For example, relaxin is originally translated in a "prepro" form that bears a prehormone sequence (thought to play a role in extrusion and possibly folding of the peptide in the endoplasmic reticulum) and a prohormone sequence comprising three regions, the so-called B, C, and A chain-coding regions (generally arrayed in that order). Post-translational processing of preprorelaxin to form mature relaxin involves the enzymatic cleavage, in its natural cellular environment, of pre- and C-region peptides to leave the B and A chain peptides, joined by disulfide bonds through cysteine residues, as well as an intra-chain disulfide bridge within the A-chain itself.

In man, relaxin is only found in one of two potential forms, designated herein as the $Asp_1$ or H2 (human 2) and $Lys_1$ or H1 (human 1) forms, corresponding to the two potential gene products in the human genome. In both forms, the A chain is devoid of Asp residues. However, in the H2 form, the relaxin B chain includes one Asp residue at position 1, whereas in the H1 form, the relaxin B chain includes Asp residues at positions 4 and 5.

There has existed a need for compositions and processes particularly adapted for the isolation of recombinant proteins that must be extensively processed through the removal of terminal and/or central peptides.

Fusion polypeptides have been prepared from appropriate microbial cloning systems that contain a methionyl residue at the fusion juncture for cleavage by cyanogen bromide. See, e.g., U.S. Pat. No. 4,356,270 issued Oct. 26, 1982. Moreover, linkers have been devised that code for an amino acid sequence representing a specific cleavage site of a proteolytic enzyme for cleavage of fusion proteins. See, e.g., U.S. Pat. No. 4,769,326 issued Sep. 6, 1988. Such processes provide recombinant technology with alternatives to eukaryotic cell expression. Further, it is known that a preferential hydrolysis of the peptide bonds of aspartyl residues occurs in dilute acid, resulting in cleavage of the peptide chain [see, e.g., Light, *Meth. Enz.* Vol. XI, p. 417–420 (1967); Ingram, *Meth. Enz.*, Vol. VI, p. 831–834 (1963); Inglis et al. in *Methods in Peptide and Protein Sequence Analysis*, Birr, ed.

(New York: Elsevier/North Holland Biomedical Press, 1980), pp. 329–343; Inglis, *Meth. Enz.*, 91, 324–332 (1983); Schroeder et al., *Biochemistry*, 2: 992–1008 (1963) (p. 1005, left column, in particular); and Schultz, *Meth. Enz.*, Vol. XI, p. 255–263 (1967)], and that preferential cleavage of aspartyl-prolyl peptide bonds takes place in dilute acid [see Marcus, *Int. J. Peptide Proteins Res.*, 25: 542–546 (1985); Piszkiewicz et al., *Biochem. Biophys. Res. Comm.*, 40: 1173–1178 (1970); Jauregui-Adell and Marti, *Anal. Biochem.*, 69: 468–473 (1975); Landon, *Meth. Enz.*, 47: 145–149 (1977)]. The Jauregui-Adell article suggests cleaving the Asp-Pro bond in the presence of strong denaturing agents to obtain reasonable yields. The Landon review article discloses that the use of guanidinium chloride is necessary to increase yields for one protein but not for another. The Inglis et al. article on p. 338 suggests that variations in amino acid sequence and environment surrounding the aspartic acid residues might affect the cleavage yields. For a thorough review of all nonenzymatic methods for preferential and selective cleavage and modification of proteins, see Witkop, in *Advances in Protein Chemistry*, Anfinsen et al., ed., Vol. 16 (Academic Press, New York, 1961), pp. 221–321, especially pp. 229–232 on aspartic acid cleavage.

UK 2,142,033 discloses cleavage of a fusion protein of IGF-I and Protein A by dilute acid treatment of a variant of the fusion protein having an Asp residue engineered at the proper fusion junction.

Despite this knowledge, there still exists a need for improved methods to produce and isolate recombinant proteins, particularly those that must be extensively processed by removal of central and terminal peptides, in high yield, and to provide for the restructuring of recombinant products into more desirable forms, for example, for the production of larger quantities of peptides having more desirable structures for expression purposes.

In recognition of these needs, it is a general object of the present invention to provide improved recombinant processes and compositions for the production of protein- or peptide-encoding DNA sequences.

It is an additional object of the present invention to provide improved processes for the production of desired proteins employing genetically engineered compositions.

It is a more particular object of the present invention to provide improved processes for providing recombinant relaxin, and in particular, human relaxin.

SUMMARY OF THE INVENTION

Accordingly, the present invention is directed to a process for cleaving a polypeptide into polypeptide cleavage products comprising treating a reduced, free-cysteine form of the polypeptide with a cleaving agent under conditions for cleaving the polypeptide at a desired junction between the polypeptide cleavage products.

In a more specific aspect, the invention provides a process for cleaving a polypeptide into polypeptide cleavage products comprising:

a) culturing cells containing DNA encoding said polypeptide, wherein an Asp codon is present in said DNA at a junction between the DNA sequences encoding the respective cleavage products, said culturing resulting in expression of the DNA to produce the polypeptide in the host cell culture; and b) treating a reduced, free-cysteine form of the polypeptide with acid at a pH of about 1 to 3 under conditions for cleaving the polypeptide at the Asp junction.

Preferably, before step (a) the cells are transformed with an expression vector comprising said DNA operably linked to control sequences recognized by the cells. Additionally preferred steps include recovering the polypeptide from the host cell culture and maintaining the recovered polypeptide under a non-oxidizing atmosphere before treatment with the acid, separating and isolating at least one of the polypeptide cleavage products after the acid treatment, and combining the isolated cleavage product with another peptidyl fragment or component, e.g., a cleavage product of the polypeptide.

In a still further aspect, the invention provides a process comprising (a) providing a polypeptide under reducing conditions whereby the cysteine residues of the polypeptide are not disulfide bonded and (b) hydrolyzing a predetermined peptide bond in the polypeptide.

In another aspect, the invention provides a process for producing biologically active human relaxin comprising the steps of:

a) providing an expression vector comprising DNA whose sequence encodes a polypeptide comprising a human relaxin A chain wherein an Asp codon is introduced at either one or both ends of the A chain, and wherein the DNA is operably linked to control sequences recognized by a host cell;

b) transforming a suitable host cell with said vector;

c) culturing the transformed cell so as to express the DNA, thereby producing a polypeptide sequence comprising the A relaxin chain;

d) recovering the polypeptide from the culture;

e) treating a reduced, free-cysteine form of the recovered polypeptide with acid at a pH of about 1 to 3 under conditions for cleaving the polypeptide at the Asp junction(s) to form cleavage products;

f) separating the cleavage products; and g) combining the A chain with a human relaxin B chain to produce biologically active human relaxin.

In other aspects the invention supplies a process for providing nucleic acid encoding a polypeptide that is desired to be cleaved comprising introducing at a desired cleavage junction codons encoding the amino acid sequence $X_n$-Y-Asp, wherein X is any one of Pro, Ala, Ser, Gly, or Glu, Y is Ala, Ser, or Gly, and n is equal to or greater than 0.

In a more specific aspect, the invention furnishes a process for providing nucleic acid encoding a variant of precursor human relaxin comprising C and A chains, which process comprises introducing codons encoding, at the C-terminus of the C chain, the sequence $X_n$-Y-, wherein X, Y and n are defined above, preferably Ser-Glu-Ala-Ala, and inserting an Asp codon between the C and A chains.

Additionally provided is a nucleic acid encoding a polypeptide that is desired to be cleaved, which nucleic acid encodes, at a desired cleavage junction, the amino acid sequence $X_n$-Y-Asp, wherein X, Y, and n are defined above.

In a more specific embodiment is provided a nucleic acid encoding a variant of precursor human relaxin comprising C and A chains, which nucleic acid comprises codons encoding, at the C-terminus of the C chain, the sequence $X_n$-Y, wherein X, Y and n are defined above, preferably Ser-Glu-Ala-Ala, and has an Asp codon inserted between the C and A chains.

Also contemplated are expression vectors comprising this nucleic acid and host cells transformed with this vector.

Additionally provided is a polypeptide that is desired to be cleaved, which polypeptide comprises, at a desired cleavage junction, the amino acid sequence $X_n$-Y-Asp, wherein X, Y, and n are defined above.

Still a further aspect of the invention is a precursor human relaxin variant comprising C and A chains, having at the C-terminus of the C chain the sequence $X_n$-Y, wherein X, Y, and n are defined above, preferably having the four C-terminal amino acids of the C chain replaced with Ser-Glu-Ala-Ala, and having an Asp residue inserted between the C and A chain.

The present invention is directed to solving the problems identified above by providing an improved means to synthesize, and process in vitro desired proteins, protein chains, or even smaller peptides. In one aspect, the invention utilizes the specific placement of Asp residue codons into protein-encoding regions of DNA molecules, which codons are expressed along with such regions into a "mutant" protein. Then, using reducing conditions and then techniques for protein cleavage that employ mild acid to cleave specifically at both the amino and carboxy moieties of Asp residues of a reduced protein, the peptidyl regions adjacent to the Asp residues are cleaved apart.

One particular use for this process is in the generation of "multi-chain" proteins such as human relaxin that exist in a native, more highly active form as A and B peptide chains, bridged together by disulfide bonds. In such embodiments, the DNA sequences encoding one peptide chain are genetically engineered to be separated from sequences that code for another chain by one or more Asp codons (GAT or GAC). Accordingly, when such a mutant protein is expressed and collected, it may be acid-treated to release the individual A chain, which itself is readily isolated to substantial purity and reconstituted in vitro with the B chain to provide a more natural protein.

The use of the process herein results in increased yields of product with maximum cleavage specificity.

Of course, the utility of the present invention is not limited to use in connection with small and/or multi-chain peptides, and numerous other uses will become apparent to those of skill in light of the present specification.

BRIEF DESCRIPTION OF THE DRAWINGS

FIG. 1 illustrates a comparison of the amino acid sequences of many of the currently known relaxin structures, with apparently conserved residues in boxes.

FIGS. 2A and 2B illustrate the protein and underlying DNA sequence of the H2 prorelaxin gene insert in plasmids pTrpProRelAsp (FIG. 2A) and pTR411 (FIG. 2B).

FIG. 3 illustrates diagrammatically the construction of plasmid pTrpProRel.

DETAILED DESCRIPTION OF THE PREFERRED EMBODIMENT

A. Definitions

Figure 4:
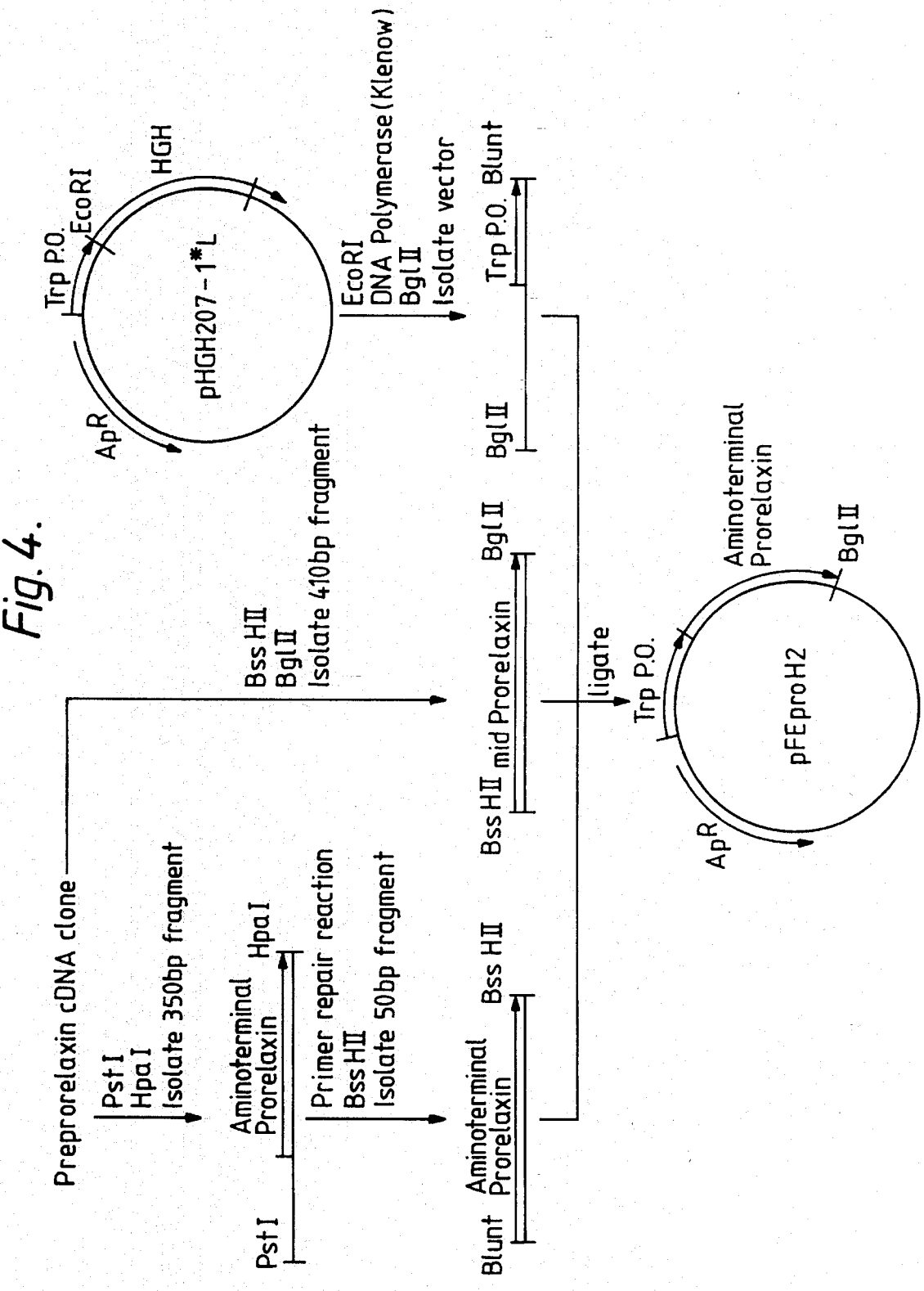
FIG. 4 illustrates diagrammatically the construction of plasmid pFEproH2.

As used herein, the term "polypeptide" signifies a polypeptide having two or more polypeptide components that are to be cleaved, such as a fusion protein. Such polypeptides include certain proteins that are expressed by recombinant means only with some difficulty. For example, certain proteins, and in particular, certain protein hormones, naturally exist in a mature form quite distinct from their cellular nascent form, requiring processing, often the action of a series of enzymes. Such proteins are said to exist in pre-, pro-, or prepro-forms, and include relaxin and insulin. Processing of such proteins generally results in the generation of two or more individual peptide chains (components), one or all of which may have biological activity, or which may themselves form bonds or crosslinks resulting in multi-chain proteins. In addition, the polypeptides herein have disulfide bonds when in an oxidized state. The preferred polypeptides herein are those that are not readily cleaved at the desired junction(s) between the components to be cleaved using a suitable cleaving agent, whether because of lack of access to the site of cleavage due to disulfide bonding, because of non-specific or auto-cleavage, or because of the amino acid environment surrounding the Asp residue. Also preferred are those polypeptides herein that contain multi-chains the internal sequence of which contains no cleavage site recognized or acted upon by the cleaving agent. For example, if the cleaving agent is acid, the polypeptide components ("cleavage products") themselves are preferably free of aspartic acid (Asp) residues that would interfere with (i.e., adversely affect or prevent) the desired cleavage (or other residues that would potentially interfere such as asparagine residues). More preferably, the components are free of internal Asp residues, and most preferably are completely devoid of Asp residues.

Numerous biologically active polypeptides that are devoid of Asp residues are known in the art. By way of illustration, proteins devoid of Asp residues include proteins such as growth-modulating peptide, eosinophilotactic factor, tuftsin, kinetensin, oxytocin, gonadoliberin, gonadotropin releasing hormone, neurotensin (bovine), bombesin, fibrinopeptide A (dog), motilin (pig), neutrophil chemotactic peptide, B-endorphin, alytesin, luteinizing hormone releasing hormone, somatostatin, substance P, litorin, thyrotropin releasing hormone, kallikrein, intrinsic factor—gastric juice, calcitonin (pig), alcohol dehydrogenase (*B. stearothermophilus*), proinsulin (pig), and interferon gamma-induced protein precursor.

While the polypeptide to be cleaved is generally any polypeptide desired for this purpose, in one preferred embodiment the polypeptides targeted for acid cleavage contain an enhanced cleavage site as defined further below, and include precursor polypeptides, e.g., prepro-, pro- or pre-forms, or mutant precursor polypeptides containing enhanced cleavage sites. Among these, more preferred are prorelaxin, preprorelaxin, prerelaxin, proinsulin, preproinsulin, preinsulin, or biologically functional analogs thereof. Yet more preferred are human prepro- or prorelaxin. The most preferred polypeptide herein is H2 prorelaxin. For the H2 prorelaxin sequence, the most preferred sequence is that containing an A chain of 24 residues, a C chain of 108 residues, and a B chain of the first 29 amino acids, i.e., it is the form of relaxin found naturally in human serum and the corpus luteum.

As used herein, the term "relaxin" refers to one of the various forms of mammalian relaxin, or to a biologically functional analog of such relaxins. Relaxin and biologically functional analogs of relaxin thus refer to a functional protein that is effective to facilitate the birth process. Remodeling of the reproductive tract is understood to include such physiological actions as ripening of the cervix; thickening of the endometrium of the pregnant uterus, as well as increased vascularization to this area; and an effect on collagen synthesis. Relaxin has also been found in the female breasts and may be associated with lactation. Moreover, relaxin has been found in seminal fluid, suggesting a role in enhancing the mobility of spermatozoa. Also, given its effect on connective tissue, relaxin may play a role in improving skin elasticity.

Assays for relaxin "biological activity" are generally known in the art and include assays for smooth muscle or uterine contractility, for relaxation of the pubic symphysis, or for measuring cyclic AMP (see, e.g., EP Publ. No. 251,615 published Jan. 7, 1988).

As used herein, the term "introduce" means the introduction into a DNA sequence of an additional codon or codons that include an Asp codon, or the alteration or mutation of an existing codon to provide an Asp codon. In this manner, a mutant protein is produced having a sequence that includes within its protein sequence the desired protein or peptide together with at least an additional Asp residue adjacent to either its amino terminus, carboxy terminus, or both. These mutant protein species may then be cleaved with mild acid treatment to release the desired protein.

As used herein, the term "reduced, free-cysteine form" refers to a form of the polypeptide that is in its reduced state, i.e., contains no disulfide bonding of cysteinyl residues that would interfere with the selective cleavage at the specific site desired, and also refers to a form that excludes the presence of other polypeptides that contain disulfide bonds, including dipeptides. For example, the prorelaxin is maintained in its reduced state without the presence of a dicysteinyl peptide with disulfide bridging. Such a peptide interferes with the cleavage even when the prorelaxin is maintained in the reduced state. Therefore, no such peptide can be present in the reaction mixture for treatment with the cleaving agent. For maintaining the polypeptide in its reduced form, thereby providing the polypeptide "under reducing conditions" as the term is used herein, any technique may be employed, including the addition of a reducing agent in a buffer containing the polypeptide, e.g., β-mercaptoethanol or the evacuation of the vessel containing the polypeptide. Dithiothreitol is contraindicated for this purpose. It is preferable, however, that the polypeptide be maintained under non-oxidizing atmospheric conditions, i.e., in the presence of a non-oxidant gas, e.g., an inert gas selected from helium, argon, neon, or krypton, or nitrogen.

As used herein, the term "cleaving agent" refers to a reagent used to cleave the polypeptide specifically so as to release its free components as desired. Suitable cleaving agents herein include enzymes, such as serine proteases, ubiquitin hydrolases, chromotrypsin, trypsin, staphylococcal protease, or subtilisin or its mutants, and chemical reagents, such as organic or inorganic acids, hydroxylamine, N-bromosuccinimide, and cyanogen bromide. Hydrolysis of peptide bonds catalyzed by a variety of proteolytic enzymes is taught in *The Enzymes*, 3rd Ed., Boyer, Ed., (Academic Press, Vol. III, 1971); *Meth. Enzymol.*, Vol. XIX, Perlmann and Lorand, Ed. (New York: Academic Press, 1970); *Meth. Enzymol.*, Vol. XLV, Lorand, Ed. (New York: Academic Press, 1976); Drapeau, *J. Biol., Chem.*, 253: 5899–5901 (1978) and Drapeau, *Meth. Enzymol.*, 47: 89–91 (1977). For an extensive listing of chemical agents, see Witcop in *Advances in Protein Chemistry*, supra, including Table III on p. 226. In addition, Asp residues can be modified to induce trypsin cleavage, as taught by Wang and Young, *Anal. Biochem.*, 91: 696–699 (1978); and cleavage as taught by U.S. Pat. 4,769,326 issued Sep. 6, 1988 to Rutter may be employed. Other cleaving agents suitable herein will be recognized by the practitioner keeping in mind the desired junction for cleavage and whether the reagent can act on the reduced form of the polypeptide.

As used herein, the term "dilute acid" refers to an acid with a molar concentration that will depend on its $pK_a$. The necessary concentration of acid is that which is sufficient to cleave a polypeptide at an Asp residue but not to cleave it at other residues where it is undesirable, and generally is such that a pH of between about 1 and about 3 is attained. Examples of suitable acids include both organic and inorganic acids such as citric acid, formic acid (for insoluble peptides), oxalic acid, acetic acid, sulfuric acid, and hydrochloric acid. Most preferred herein are acetic acid, hydrochloric acid, and sulfuric acid, most preferably acetic acid. In a typical protocol, the expressed protein is treated with acetic acid on the order of between about 0.1 to 1.0M for about 4 to 24 hours at about 90° to 120° C.

"Mildly hydrolytic conditions" refer to cleavage conditions that result in hydrolysis only of the desired peptide bond(s). Thus, the hydrolytic conditions must be commensurate with sufficient peptide bond cleavage at the desired site, and more preferably a pH of about 1 to 3 for acid cleavage at aspartic acid residues.

B. Modes for Carrying Out the Invention

1. Introduction of Cleavage Recognition Codons into DNA Sequences

For the cleavage process, once a desired polypeptide is selected for production in accordance with this invention, it may be necessary to alter the gene sequence for the desired protein to introduce the codon(s) needed for recognition by the cleaving agent at an appropriate position or positions. Typically, where the desired polypeptide has no such residues within its sequence, it will be necessary to insert the appropriate codons either upstream and preferably adjacent to the 5'-terminal codon of the sequence encoding the desired polypeptide (where the carboxy terminus of the desired peptide is also the carboxy terminus of the expected translation product), downstream, and preferably adjacent the carboxy terminal codon of the desired component of the polypeptide (where the amino terminus of the desired polypeptide is also the amino terminus of the expected translation product), or both (where the desired polypeptide component to be isolated is an internal polypeptide of the expected translation product).

Of course, where the expected translation product naturally includes an internal or terminal residue recognized by the cleaving agent, it will generally be necessary to introduce only one such codon coding for that residue, at a position upstream or downstream and adjacent the region to be isolated. Thus, for example, where a polypeptide component naturally includes an Asp residue within its amino-terminal region (i.e., the amino-terminal half) or within its carboxy-terminal region (i.e., the carboxy terminal half), it will generally be desirable to introduce an Asp residue upstream and adjacent the carboxy terminus or amino terminus, respectively, depending on the peptidyl region ultimately sought to be prepared.

Preferably, a cleavage site for recognition by the acid is a sequence that enhances the cleavage, such as the sequence $X_n$-Y-Asp, where X is any one of Ala, Ser, Glu, Pro, or Gly, Y is Ala, Ser, or Gly, and n is greater than or equal to 0. Examples of such sequences include Ser-Glu-Ala-Ala-Asp, and conservative amino acid substitutions thereof, such as Ala-Glu-Ala-Ala-Asp, Ser-Glu-Ser-Ala-Asp, Ser-Glu-Ser-Ser-Asp, etc.

The sequence Ser-Glu-Ala-Ala-Asp was chosen for the example below because it represents an internal sequence of the C chain of human H2 relaxin that was found to be cleaved quite readily. Thus, in a preferred embodiment, a variant of precursor human H2 relaxin is prepared that has the four C-terminal amino acids of the C chain replaced with the codons encoding the sequence Ser-Glu-Ala-Ala- and the C chain connected to the A chain via an Asp residue. It will be understood, however, that the B and C chains of human relaxin are carrier polypeptides and that other polypeptides than those derived from human prorelaxin can be attached to the human relaxin A chain via an enhanced acid cleavage site such as that described above.

In another preferred embodiment, several polypeptide chains (e.g., human relaxin A chains) are prepared simultaneously by constructing DNA encoding multiple (at least two) polypeptide cleavage product chains separated by Asp codons. Preferably such multiple chain segment has the sequence:

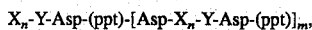

wherein ppt is a polypeptide cleavage product (a polypeptide component resulting from cleavage of a desired peptide bond of the polypeptide), m is greater than or equal to 0, and n, X, and Y are defined above. Preferably, m is greater than or equal to 1, more preferably 2 or 3, and n is 0–10, and more preferably about 3. Also, preferably the polypeptide cleavage product is free of Asp residues, and is more preferably relaxin A chain, and most preferably human H2 relaxin A chain. Most preferably the chain segment has the sequence:

wherein m is defined above, most preferably 2 or 3, and Rlx A is relaxin A chain, most preferably human H2 relaxin A chain.

Introduction of one or more particular codons into selected regions of a DNA sequence, whether by codon insertion or by altering existing codons, is readily achieved employing methods well known in the art. One such method is referred to as site-directed in vitro mutagenesis (Boller et al. (1982), *Nucl. Acids Res.*, 10: 6487–6500). In this method, a single-stranded template of the starting DNA sequence is prepared using the M13 phage system. Then, short single-stranded primer sequence, generally about 12 to 100 nucleotides in length, is prepared synthetically (e.g., by the H-phosphonate method of Froehler et al. (1986), *Nucl. Acids Res.*, 14: 5399–5407, the disclosure of which is incorporated herein by reference). This synthetically prepared primer will include the sequence desired for the mutated DNA, that is, the primer encodes a DNA sequence complementary to the template but also including the desired codon(s) at the desired replacement point(s). After the primer is annealed to the template, the primer is extended using a DNA polymerase (e.g., *E. coli* DNA polymerase, Klenow fragment) to provide a double-stranded DNA molecule, with one strand bearing the original sequence and the other strand bearing the desired "mutated" sequence.

This construction is then employed to transform an appropriate M13 host (e.g., *E. coli* JM101), in which certain offspring will bear the desired "mutated" sequence and certain offspring will bear the original starting sequence. Those offspring bearing the mutated sequence may then be selected by conventional techniques. The isolated construct may then be manipulated as desired to express the resultant mutant protein in an appropriate host.

Another method that may be employed to introduce the desired codon(s) is by simple restriction enzyme fragment replacement. For this approach, it is generally desirable to identify first a unique restriction fragment that spans the gene region to be altered. This is a conventional technique, requiring only knowledge of the location of restriction sites surrounding the sequence to be engineered. From the known DNA sequence, restriction sites are ascertained, most simply through the use of a computer program that compares the sequence to a catalog of enzyme specificities. From the known restriction map, one must then identify a fragment that spans the DNA region where the desired codon(s) are to be inserted. Preferably, this fragment is "unique" in the sense that the remaining portion of the vector remains intact when the fragment is digested free of the vector. However, unique fragments of manageable length are often unavailable or not practicable. In such cases, one will generally desire to employ the fragment resulting in least vector fragmentation.

A corresponding replacement double-stranded DNA fragment bearing the original sequence but with the desired codon(s) introduced at an appropriate point is then prepared, generally synthetically. This replacement fragment bearing the mutant sequence is preferably prepared having appropriate restriction "sticky ends" (or blunt ends as the case may be), such that the mutant fragment may be readily annealed with the digested gene sequences so as to replace the excised portion. After the synthetic fragment is annealed with the vector fragment, thus effectively replacing the original fragment, appropriate host cells are transformed and selected.

Regardless of the method employed for the introduction of such residues, a mutated DNA sequence bearing the appropriate codon insertions is obtained, which sequence may then be expressed in an appropriate host, whether prokaryotic or eukaryotic. The vectors and method disclosed herein are suitable for use in host cells over a wide range of prokaryotic and eukaryotic organisms.

2. Exemplary Cloning Systems and Methodology a. Vectors and Hosts

In general, of course, prokaryotes are preferred for cloning of DNA sequences and for constructing the vectors useful in the invention. For example, *E. coli* K12 strain 294 (ATCC No. 31,446) and its derivative *E. coli* MM294tonA (resistant to T1 phage and obtained generally by transduction using the protocol described in EP 183,469 published Jun. 4, 1986) is particularly useful. Other microbial strains that may be used include *E. coli* strains such as *E. coli* B and *E. coli* X1776 (ATCC No. 31,537). In the case of M13 phage cloning, the preferred host is generally *E. coli* JM101. Prokaryotes may also be used for expression. The aforementioned strains, as well as *E. coli* W3110 (F⁻, lambda, prototrophic, ATCC No. 27,325), bacilli such as *Bacillus subtilus*, and other enterobacteriaceae such as *Salmonella typhimurium* or *Serratia marcesans*, and various pseudomonas species may be used. These examples are, of course, intended to be illustrative rather than limiting, as numerous bacterial strains for expression and other purposes are well known and widely available to those of skill in the art.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species [Bolivar et al., *Gene*, 2: 95 (1977)]. pBR322 contains genes for ampicillin and tetracycline resistance and thus provides easy means for identifying transformed cells. The pBR322 plasmid, or other microbial plasmid, must also contain, or be modified to contain, promoters that can be used by the microbial organism for expression of its own proteins. Those promoters most commonly used in recombinant DNA construction include the beta-lactamase (penicillinase) and lactose promoter systems [Chang et al., *Nature*, 275: 615 (1978); Itakura et al., *Science*, 198: 1056 (1977); Goeddel et al., *Nature*, 281: 544 (1979)] and a tryptophan (trp) promoter system [Goeddel et al., *Nucleic Acids Res.*, 8: 4057 (1980); EPO Appl. Publ. No. 36,776]. While these are the most commonly used, other microbial promoters have been discovered and utilized, and details concerning their nucleotide sequences have been published, enabling a skilled worker to ligate them functionally with plasmid vectors [Siebenlist et al., *Cell*, 20: 269 (1980)].

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in Saccharomyces, the plasmid YRp7 [Stinchcomb, et al., *Nature*, 282: 39 (1979); Kingsman et al., *Gene*, 7: 141 (1979); Tschemper et al., *Gene*, 10: 157 (1980)], for example, is commonly used. This plasmid already contains the trpl gene that provides a selection marker for a mutant strain of yeast lacking the ability to grow in tryptophan, for example, ATCC No. 44,076 or PEP4-1 [Jones, *Genetics*, 85: 12 (1977)]. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase [Hitzeman et al., *J. Biol. Chem.*, 255: 2073 (1980)] or other glycolytic enzymes [Hess et al., *J. Adv. Enzyme Reg.*, 7: 149 (1968); Holland et al., *Biochemistry*, 17: 4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, supra). Any plasmid vector containing yeast-compatible promoter, origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and WI38, BHK, COS-7, and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication [Fiers et al., *Nature*, 273: 113 (1978)]. Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., polyoma, adeno, VSV, BPV) source, or by the host cell chromosomal replication mechanism. If the vector is integrated into the host cell chromosome, the latter is often sufficient.

Examples that are set forth hereinbelow describe use of *E. coli* using trp promoter systems. However, it would be well within the skill of the art to use analogous techniques to construct expression vectors for expression of desired protein sequences in alternative prokaryotic or eukaryotic host cell cultures.

b. Exemplary Laboratory Techniques

If cells without formidable cell membrane barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells that contain substantial cell wall constructions are used, the preferred method of transfection is calcium treatment using calcium chloride as described by Cohen et al., *Proc. Natl. Acad. Sci. U.S.A.*, 69: 2110 (1972).

Construction of suitable vectors containing the desired coding and control sequences employs standard ligation techniques. Isolated plasmids or DNA fragments are cleaved, tailored, and religated in the form desired to prepare the plasmids required.

Cleavage of DNA is performed by treating with restriction enzyme (or enzymes) in suitable buffer. In general, about 1 µg plasmid or DNA fragments is used with about 1 unit of enzyme in about 20 µl of buffer solution. (Appropriate buffers and substrate amounts for particular restriction enzymes are specified by the manufacturer.) Incubation times of about one hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° C. with 10 units of Polymerase I (Klenow), phenolchloroform extracted, and ethanol precipitated.

Size separation of the cleaved fragments is performed using 6 percent polyacrylamide gel described by Goeddel et al., *Nucl. Acids. Res.*, 8: 4057 (1980).

For ligation, approximately equimolar amounts of the desired components, suitably end-tailored to provide correct matching, are treated with about 10 units T4 DNA ligase per 0.5 µg DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform *E. coli* K12 strain 294 (ATCC 31,446), or a derivative thereof, and successful transformants are selected by ampicillin or tetracycline resistance where appropriate. Plasmids from the transformants are prepared, analyzed by restriction mapping, and/or sequenced by the method of Messing et al., *Nucl. Acids Res.*, 9: 309 (1981) or by the method of Maxam et al., *Meth. Enzymol.*, 65: 499 (1980).

3. Cleavage of Reduced Polypeptides

Whether or not the polypeptide is obtained by recombinant DNA technology, it is subjected to treatment with the appropriate cleaving agent. If the polypeptide is recombinantly expressed, as is preferred, it is preferably recovered from the host cell culture, as by lysing the cells and centrifuging them to obtain the appropriate fraction containing the polypeptide, and optionally purified from that fraction using techniques for recovering proteins from inclusion bodies, and placed in a buffer, before it is treated with the cleaving agent. In any event, for substantial increase in product yields, the polypeptide must be in reduced form before it is exposed to the cleaving agent, as shown by the accompanying examples. As mentioned above, the maintenance in reduced form is accomplished by any number of techniques, such as adding a reducing agent to the polypeptide and purging the container of oxygen before exposure to the cleaving agent as by purging with a non-oxidant gas such as argon, helium, or nitrogen.

The polypeptide is then treated with the cleaving agent under conditions resulting in the release of the desired peptide or peptides contained therein. Treatment will depend of course on the cleaving agent employed, and the conditions will be readily apparent to one skilled in the art given the cleaving agent employed. Examples of various cleaving agents and conditions associated with each can be found in Witkop in *Advances in Protein Chemistry*, supra.

Generally speaking, hydrolysis at Asp residues is achieved by heating the polypeptide for a period of time in dilute acid in accordance with the procedure of Schultz (1967), *Methods Enzymol.*, 11: 255–263; Light (1967), *Methods Enzymol.*, 11: 417–420; both incorporated herein by reference. However, it may be appropriate to modify these conditions under certain circumstances, taking into consideration the partial pressure (presence) of oxygen, protein concentrations that might range from about 0.1 to 1 mg/ml (higher amounts are deleterious to yields), the purity of the desired starting material, and potential chemical side reactions of a less desirable nature.

Accordingly, depending on the protein being cleaved, acetic acid concentrations may range from about 0.1N to 1.0N, HCl concentrations from about 0.01N to 0.1N, or sulfuric acid concentrations from about 0.001 to 0.1N. Moreover, for acetic acid or HCl incubation times will range from about 2 to 10 hours, and temperatures from about 90° to 120° C., and for sulfuric acid incubation times will range from 1–8 hours, and temperatures from about 85° to 130° C. More preferably, acetic acid concentrations will range from about 0.25 to about 0.75N (or HCl from about 0.025N to about 0.05N, or sulfuric acid from about 0.003N to about 0.01N), with incubation times of about 4 to 8 hours for acetic acid and HCl and of about 2 to 4 hours for sulfuric acid, at from about 100° to about 115° C. Most preferably, an acetic acid concentration of about 0.5N is chosen (or about 0.05N HCl or about 0.005N sulfuric acid) with an incubation time of about 4 hours and an incubation temperature of about 110° C.

In a typical protocol, found to work well in connection with the cleaving of mutant prorelaxin discussed below, samples of the expressed, relatively purified mutant protein are diafiltered into a urea buffer containing β-mercaptoethanol purged with helium or argon gas and diafiltered within 0–48 hours after the first diafiltration against acetic acid. After diafiltration, the sample is heated to about 110° C. for about 2 to 10 hours, typically about 4–8 hours, at a protein concentration of about 0.25 to 1.0 mg/ml, and then the A chain is isolated and purified.

Purification of cleavage products is obtained by one of numerous peptide purification techniques, including, for example, gel or paper electrophoresis, chromatography, gradient centrifugation, and the like. It has been found that high performance liquid chromatography (HPLC) works particularly well in the separation and purification of acid-cleaved peptides.

4. Chain Combination

The relaxin chains can be combined using the method taught in EP Pub. No. 251,615, supra, the disclosure of which is incorporated herein by reference. Briefly, the application teaches a method of combining the A and B chains of human relaxin comprising mixing the reduced, free-cysteine form of the A chain and the reduced, free-cysteine form of the B chain in an aqueous medium having a pH of from about 7.0 to 12 under exposure to oxygen, under conditions whereby the B chain, but not the relaxin product, is denatured.

4. Formulation

The human relaxin can be formulated using known methods to prepare pharmaceutically useful compositions such that the human relaxin is combined with a pharmaceutically acceptable carrier. Suitable vehicles and their formulation, including other necessary human proteins, e.g., human serum albumin, are described in standard formulation treatises, e.g., Remington's *Pharmaceutical Sciences* by E. W. Martin. Preferably, the human relaxin is formulated as described in U.S. Ser. No. 07/303,779 filed Jan. 27, 1989, the disclosure of which is incorporated herein by reference. Briefly, for a liquid formulation useful particularly for systemic administration, the relaxin is contained in an effective amount in a buffer capable of maintaining the pH of the composition at about 4 to below about 7. If the formulation is designed for topical applications, including intracervical or intravaginal application, the relaxin is conveniently provided in a gel format. Suitable vehicles for the gel include such agents as water-soluble polysaccharides such as, e.g., methylcellulose or polyethylene glycol. If the gel is light sensitive, it must be stored under conditions that avoid exposure to light or in the presence of a proper stabilizer.

The examples that follow demonstrate the use of the present invention in connection with recombinant plasmids that encode relaxin proteins that are readily acid-cleaved to provide purified A chain protein. The methods employed herein are exemplary only. It will be apparent that various departures from and modifications of these techniques may be made in light of the present specification and the ordinary level of skill in the art without departing from the spirit and scope of the invention. All literature and patent citations in the examples are expressly incorporated by reference.

EXAMPLE 1

Construction of Recombinant Vectors That Encode Asp-Inserted Human Prorelaxin

A recombinant plasmid, designated pTR411, was constructed that encoded an Asp-inserted mutant of human H2 prorelaxin. This plasmid was prepared starting with a parental plasmid encoding H2 prorelaxin, designated pTrpProRelAsp, whose preparation proceeded through various intermediates. The end product of this genetic engineering was plasmid pTR411, which included the sequence of H2 prorelaxin DNA having an additional Asp codon inserted between the codons for amino acids $Leu_{33}$ and $Ser_{34}$, and $Arg_{137}$ and $Gln_{138}$. Both the protein and underlying DNA sequences of plasmids pTrpProRelAsp and pTR411 are displayed in FIGS. 2A and 2B, respectively.

A. Preparation of Plasmid pTrpProRelAsp

The preparation of the parental plasmid, pTrpProRelAsp, proceeded through a number of intermediates, including first plasmid pTrpProRel followed by pTrpStIIProRel. pTrpProRel is a plasmid that was constructed to include the Trp promoter and a methionine codon in front of a prorelaxin H2-encoding DNA sequence. pTrpStIIProRel was constructed to include the StII leader sequence (U.S. Pat. No. 4,680,262). pTrpProRelAsp was then prepared from pTrpStIIProRel through the removal of the StII leader sequence and the first 11 amino acids of H2 prorelaxin (starting with $Ser_1$) and its replacement with a sequence encoding Met-$Asp_1$ followed by amino acids 2–12 of H2 prorelaxin.

1. pTrpProRel

Referring to FIG. 3, it can be seen that plasmid pTrpProRel was constructed in two steps. The first step introduced the Trp promoter and a methionine codon in front of the first half of the prorelaxin coding sequence, followed by adding on the back half of the prorelaxin gene.

The first step, as depicted in FIG. 4, was accomplished by the ligation of the three fragments to form plasmid pFEproH2. The first of the three fragments, a blunt-end/BssHII fragment encoding amino acids 1 to 16 of Met prorelaxin, was prepared by primer extension using a 350 basepair PstI/HpaI fragment template isolated from the original cDNA clone (see, e.g., U.S. Pat. No. 4,758,516 and Hudson et al., *EMBO Jrnl.* 3: 2333–2339 (1984)).

Briefly, the original cDNA clone was isolated as follows: Samples of human corpus luteum were made available as a result of surgical intervention in ectopic pregnancies or from lutectomy at the time of Caesarian section. From the RNA isolated from a single corpus luteum a cDNA library was constructed in pBR322 providing about 300 unique recombinant plasmids. This library was screened with an H1-cDNA probe corresponding to a 400 nucleotide segment coding for the C- and A-chains from amino acid 64 through the termination codon and including 80 bases of the 3' untranslated region. A single positive cDNA clone from the pBR322 library was isolated and sequenced and found to have sequence homology to human relaxin H1. The total number of recombinant clones from such small amounts of ovarian tissue was increased by constructing cDNA libraries using the λGT10 cloning system. Screening with a relaxin-specific probe identified 23 unique cDNA clones of which six were characterized as shown in FIG. 1 of U.S. Pat. No. 4,758,516. Nucleotide sequence analysis revealed that all six cDNA recombinant clones encoded fragments of the same relaxin structural gene, yet this sequence was different from that of the genomic H1 clone.

The cDNA clone shown in FIG. 1 of U.S. Pat. No. 4,758,516 and identified as a, b, or c was digested with PstI and HpaI. The resulting PstI/HpaI fragment and the 15-mer primer 5'-ATGTCATGGATGGAG, which encoded the amino acids Met-Ser-Trp-Met-Glu, were employed in a primer repair reaction (see, e.g., U.S. Pat. No. 4,663,283) to create the blunt-end/BssHII fragment.

The second piece was a 410 basepair BssHII/BglII fragment containing codons 17 to 153 of prorelaxin isolated from the original cDNA clone shown in FIG. 1 of U.S. Pat. No. 4,758,516.

The third piece was a cloning vehicle that was prepared from plasmid pHGH207-1*L by treating it with EcoRI, DNA polymerase (Klenow fragment) and then BglII. [pHGH 207-1*L is identical to pHGH207 (U.S. Pat. No. 4,663,283, incorporated herein by reference), except that the EcoRI site upstream of the Trp promoter had been removed by EcoRI digestion and blunting with DNA polymerase Klenow.] This removed a 420 basepair fragment encoding the first 137 amino acids of metHGH, leaving the cloning vector intact. This fragment included resistance genes for ampicillin and tetracycline.

The ligation mixture was used to transform *E. coli* K12 strain 294. Colonies were selected for ampicillin resistance and screened by colony hybridization using the 15-mer disclosed above. Positive clones were identified by M13 dideoxy sequencing.

As shown in FIG. 3, the second step results in the formation of plasmid pTrpProRel. For this construction, a three-piece ligation was employed. The first segment was a 1510 basepair PstI/BglII fragment from pFEproH2 that contained the amino-terminal half of the H2 prorelaxin coding sequence. The second was a 100 basepair AvaII/BglII fragment from the original cDNA clone (Hudson et al., supra) in which the AvaII site had been blunted by treatment with DNA polymerase (Klenow). This fragment contained the last 6 codons of prorelaxin. The third was pBR322XAP that had been treated with EcoRI, DNA polymerase (Klenow) and PstI to remove the 750 basepair fragment encoding the front half of the β-lactamase gene [pBR322XAP is a derivative of pBR322 in which the 640 basepair AvaI/PvuII fragment has been removed.]

The ligation mixture was used to transform *E. coli* strain 294, and colonies were selected by tetracycline resistance and screened by restriction analysis.

2. pTrpStIIProRel

Figure 5:
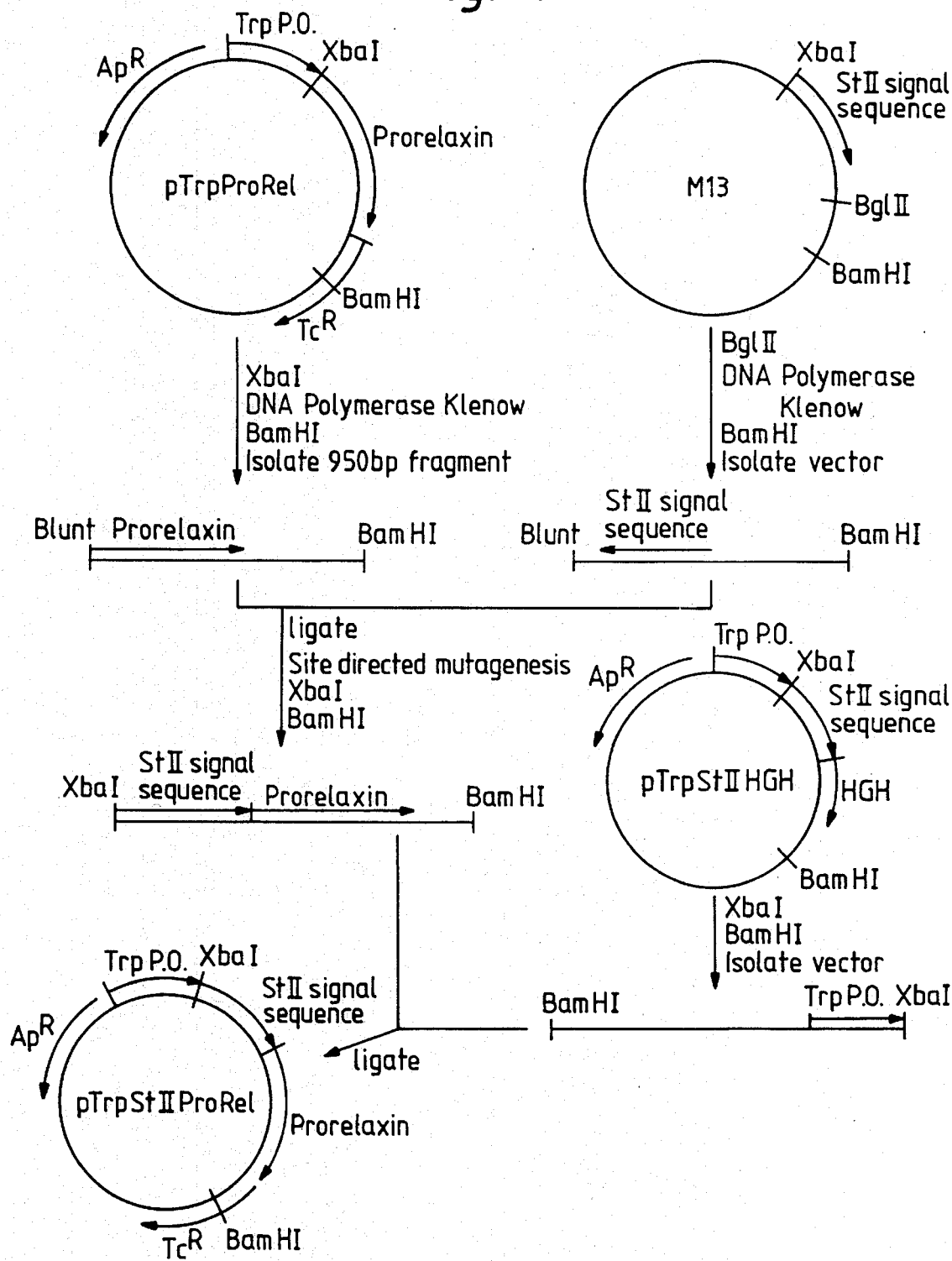
FIG. 5 illustrates diagrammatically the construction of plasmid pTrpStIIProRel.

The plasmid pTrpStIIProRel was an intermediate in the construction of pTrpProRelAsp. As shown in FIG. 5, pTrpStIIProRel was constructed in two steps, the first of which involved M13 site-directed mutagenesis wherein the prorelaxin coding sequence was fused precisely to that of the StII signal sequence. This was accomplished by ligating a 950 basepair XbaI/BamHI fragment from pTrpProRel in which the XbaI site had been blunted with DNA polymerase (Klenow) into an M13 phage vector containing the StII signal sequence with an XbaI site just upstream of the ATG codon. The M13 vector was previously treated with BglII, DNA polymerase (Klenow), and then BamHI. Standard procedures were then followed for site-directed mutagenesis (see, e.g., Adelman et al. (1983), *DNA*, 2: 183).

After identification of the correct M13 clone, the 1020 basepair XbaI/BamHI fragment encoding the StII signal sequence fused precisely to the prorelaxin gene was excised and ligated into a vector identical to pTrpStIIHGH (U.S. Pat. No. 4,680,262, incorporated herein by reference) in which the 1000 basepair XbaI/BamHI fragment encoding the HGH gene had been removed.

3. pTrpProRelAsp

Figure 6:
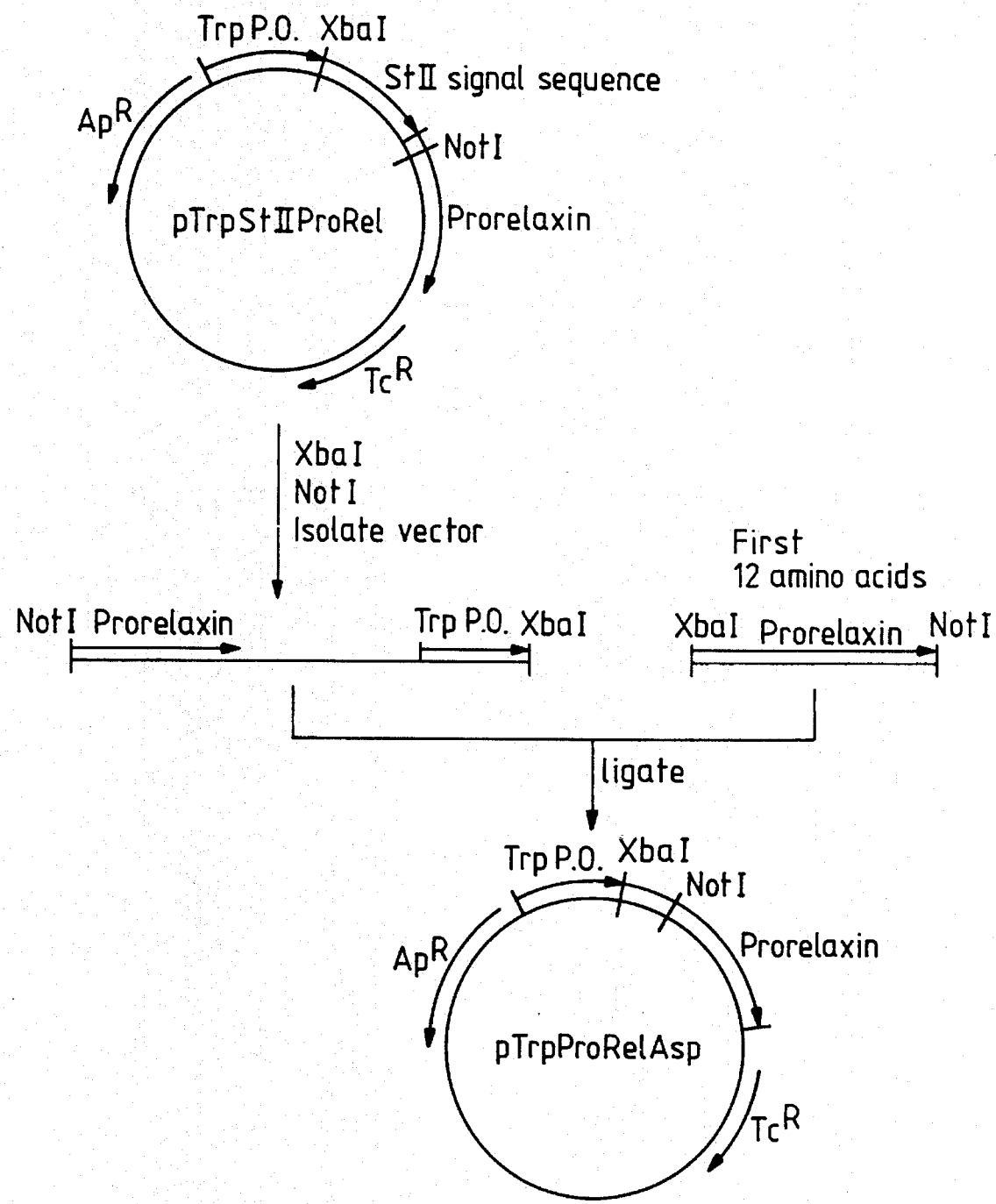
FIG. 6 illustrates diagrammatically the construction of plasmid pTrpProRelAsp.

Referring to FIG. 6, it can be seen that plasmid pTrpProRelAsp was prepared from plasmid pTrpStIIProRel through the removal of a 105 basepair XbaI/NotI fragment containing the StII sequence and the first 11 amino acids of H2 prorelaxin. This fragment was replaced with the following synthetically produced DNA duplex:

5'-CTAGAATTATGGACTCTTGGATGGAA-
GAAGTTATCAAACTGTGC TTAATACCTGAGAACCTAC-
CTTCTTCAATAGTTTGACACGCCGG-5'

As will be appreciated, this synthetic sequence encoded the first 12 amino acids of H2 prorelaxin (including $Asp_1$ of prorelaxin).

This construction was used to transform *E. coli* strain 294, and colonies were selected by tetracycline resistance.

B. Preparation of Plasmid pTR411

Figure 9:
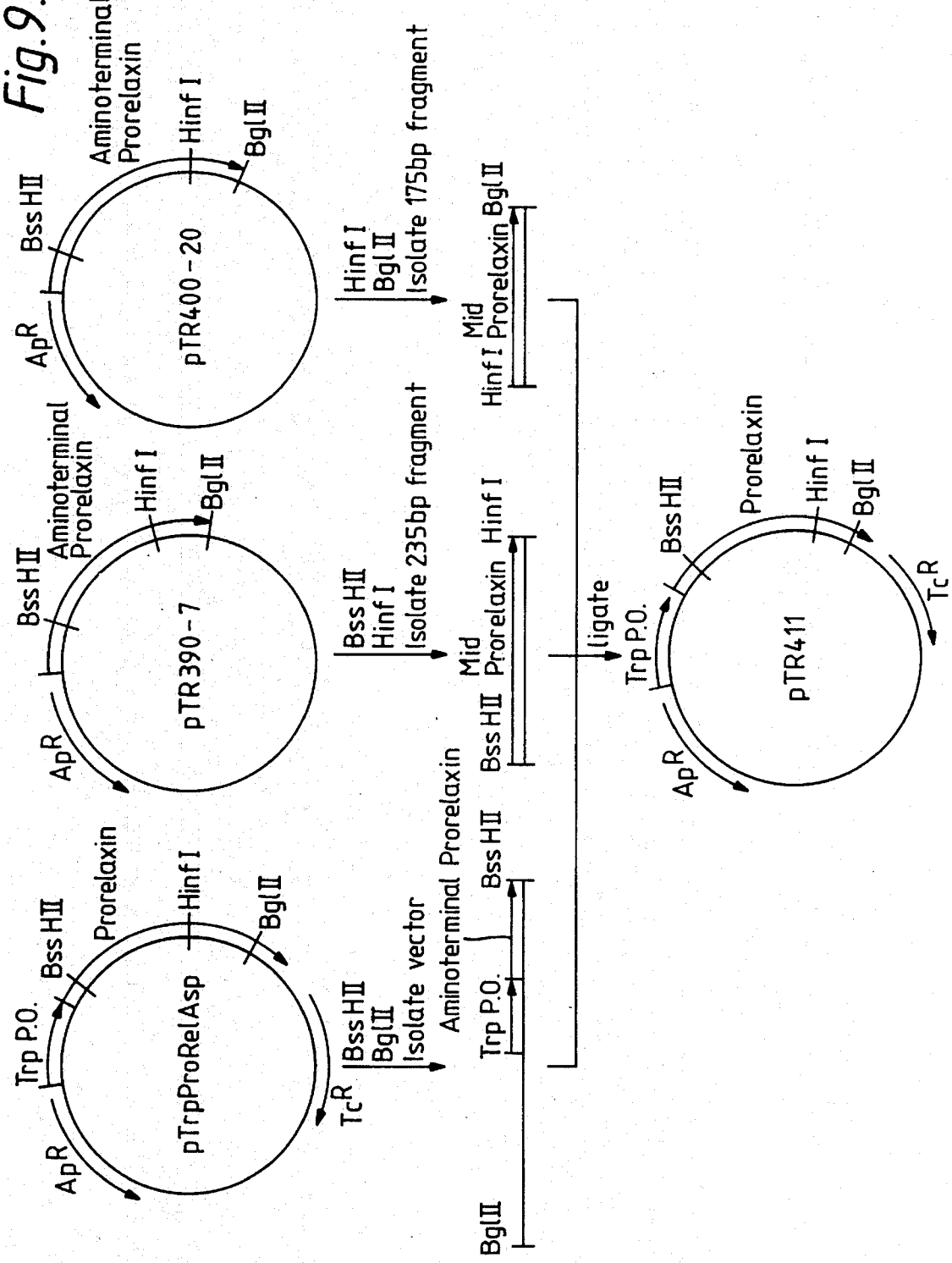
FIG. 9 illustrates diagrammatically the construction of plasmid pTR411 from fragments of pTR390-7, pTR400-20, and pTrpProRelAsp.

Plasmid pTR411 was constructed from three plasmids in all, the parental plasmid pTrpProRelAsp and two plasmids, pTR390-7 and pTR400-20, designed to provide Asp-codon-engineered replacement fragments for the regions spanning the B/C and C/A interface, respectively. The overall scheme employed in the construction of plasmid pTR411 is shown in FIG. 9.

1. pTR390-7

Figure 7:
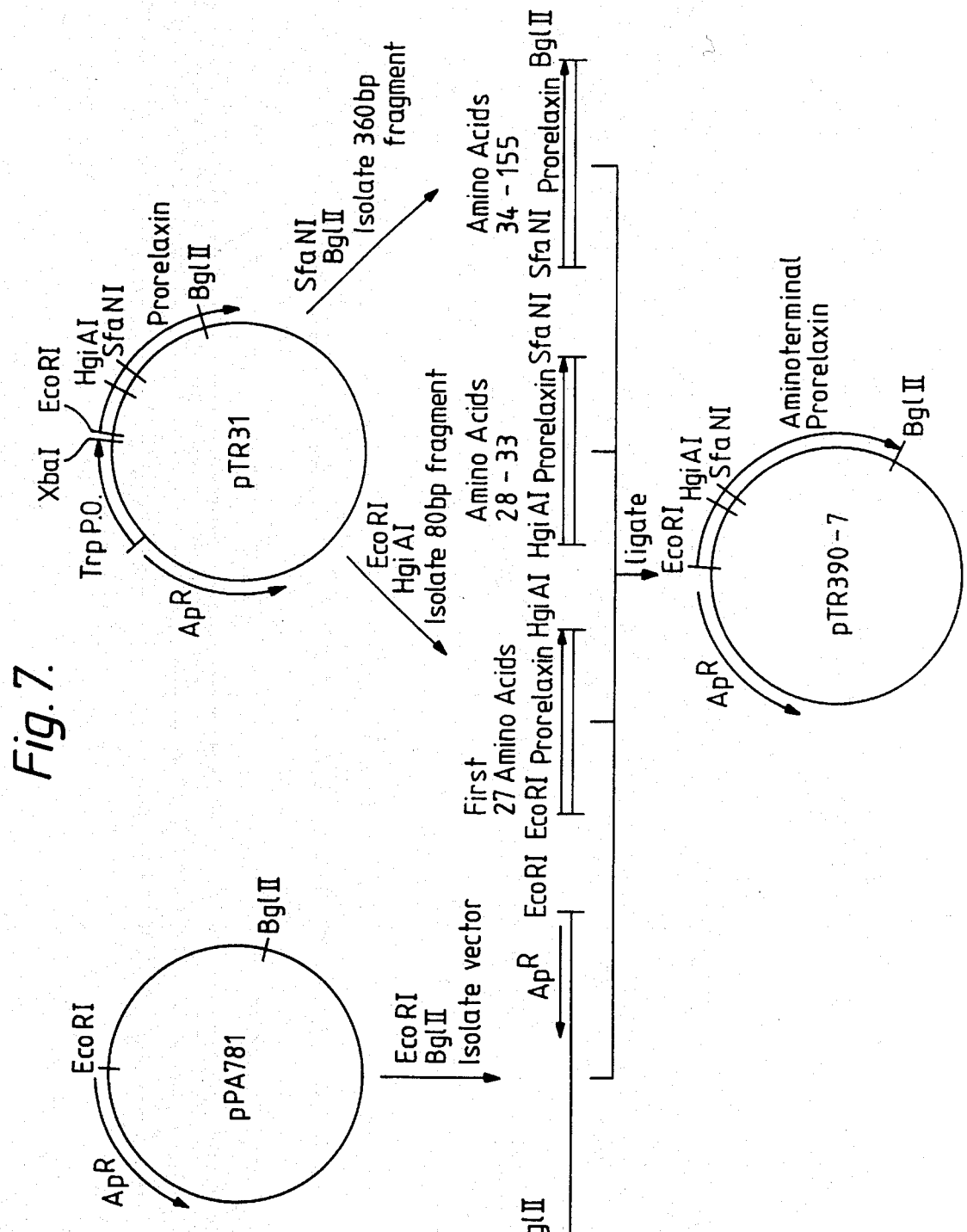
FIG. 7 illustrates diagrammatically the construction of plasmid pTR390-7.

Plasmid pTR390-7 was designed to introduce an Asp codon in the Met-prorelaxin gene between the end of the B-chain encoding and start of the C-chain encoding DNA sequences. As can be seen in FIG. 7, plasmid pTR390-7 was constructed by the ligation of four fragments, the first of which was simply a cloning vector (pPA781; see below) in which a nonessential EcoRI-BglII fragment had been removed. The insert for this cloning vector was comprised of three fragments. The first was an 80-basepair EcoRI-HgiAI fragment from pTR31 which contained the first 27 codons of Met-prorelaxin. pTR31 is a derivative of pTrpProRelAsp in which the 40 basepair XbaI/NotI fragment had been replaced with the synthetic DNA duplex:
5'-CTAGAATTCTATGGACAGTTGGATGGAA-
GAAGTGATCAAGTTGTGT TTAAGATACCTGT-
CAACCTACCTTCTTCACTAGTTCAACACACCGG-
5'.

The second fragment was a 360 basepair SfaNI-BglII fragment, also from pTR31, which contained codons 34–155 of Met-prorelaxin, and the third fragment a synthetic DNA duplex having the sequence:
5'-CCTGGAGCAAAAGGTCTCTGGAT TCGTGGAC-
CTCGTTTTCCAGAGACCTATCGG-5'

As will be appreciated, the above sequence encodes amino acids 28 through 33 of prorelaxin followed by the Asp codon GAT. This synthetic fragment was prepared generally by the triester method (Crea et al., supra).

[pPA781 is a derivative of the plasmid JH101 (*Jrnl. Bacteriol.*, 154: 1513–1515 (1983)). The 29 basepair EcoRI-HindIII fragment from this plasmid had been replaced with an 810 basepair DNA fragment containing the Pac promoter (*Proc. Natl. Acad. Sci. USA*, 81: 439–443 (1984)), *Bacillus amyloliquifaciens* alpha-amylase signal sequence (*Gene*, 15: 43–51 (1981)), and the human growth hormone gene (*Nature*, 281: 544–548 (1979)).]

The four fragments were ligated together and used to transform *E. coli* cells. Transformants were selected on ampicillin and the plasmid pTR390-7 was selected by restriction analysis and dideoxy sequencing.

2. pTR400-20

Figure 8:
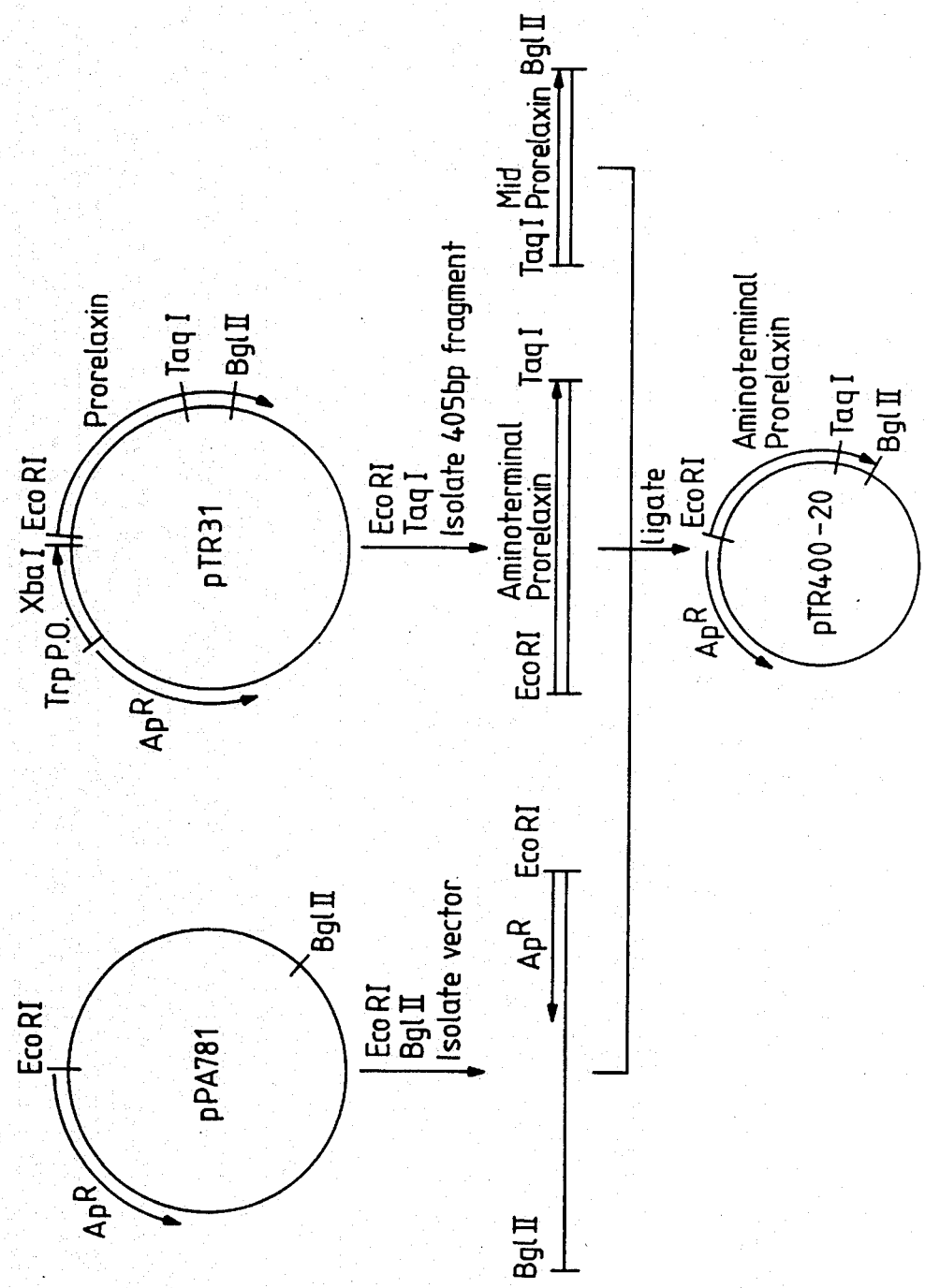
FIG. 8 illustrates diagrammatically the construction of plasmid pTR400-20.

Plasmid pTR400-20 was designed to introduce an Asp codon in the Met-prorelaxin gene between the end of the C-chain ($Arg_{137}$) and beginning of the A-chain ($Gln_{138}$) encoding regions. As can be seen in FIG. 8, this plasmid was constructed by ligating together three fragments. As with pTR390-7, the first fragment was simply a cloning vector (pPA781) in which the nonessential EcoRI-BglII fragment had been removed. The second fragment was a 405 basepair EcoRI-TaqI fragment containing codons 1–134 of Met-prorelaxin obtained from plasmid pTR31 by EcoRI-TaqI digestion. The third piece was a synthetic DNA duplex, synthesized in the manner discussed above, and having the sequence:
5'-CGAAAAAAGAGAGATCAACTCTACAGTGCATT-
TTTTTCTCTCTAGTTGAGATGTCACGTAA-
GGCTAATAAATGTTGCCATGTTGGTTG-
TACCAAAA CCGATTATTTACAACGGTACAAC-
CAACATGGTTTTCTAG-5'

As will be appreciated, the above synthetic fragment encodes amino acids 135–154 of Met-prorelaxin, with the addition of an Asp codon (GAT) between amino acid codon 137 (AGA) and 138 (CAA).

The three fragments were ligated together and used to transform *E. coli* K12 strain 294 cells. Transformants were selected by ampicillin resistance and plasmid pTR400-20 was selected by restriction analysis and subjected to dideoxy sequencing.

3. pTR411

Referring to FIG. 9, plasmid pTR411 was constructed by ligating together three pieces of DNA. The first piece was plasmid pTrpProRelAsp in which the 410 basepair BssHII-BglII fragment had been removed. This linearized plasmid therefore contained codons for amino acids 1–18 and 156–161 of prorelaxin. The second piece was a 235 basepair BssHII-HinfI fragment from pTR390-7 that contained the codons for amino acids 19–97, with an additional Asp codon between the codons for amino acids 33 (leu) and 34 (ser). The third piece was a 175 basepair HinfI-BglII fragment from pTR400-20 that contained codons 99–155 of met-prorelaxin, with an extra Asp codon between the codons for amino acid 137 (arg) and 138 (gln).

After ligation of the three fragments, the mixture was employed to transform E. coli K12 strain 294 cells. Transformants were selected by ampicillin resistance, and plasmid pTR411 was selected by restriction analysis.

```
5
AATTCCGCGGAAAGCAGTCCTTCAGAATTAAAATACTTAGGCTTGGAAACTCATTCTTCAGAGGC-
3
GGCGCCTTTCGTCAGGAAGTCTTAATTTTATGAATCCGAACCTTTGAGTAAGAAGTCTCCG-

AGCT-3'
TCGACTAG-5'
```

EXAMPLE 2

Construction of Recombinant Vectors That Encode Asp-Inserted Human Prorelaxin With Enhanced Acid Cleavage Site The plasmid pTR601 (FIG. 13) is a derivative of pTR411 (FIG. 9) in which the prorelaxin encoding sequence has been changed to produce a protein with an enhanced acid cleavage site preceding the relaxin A chain. Codons for amino acids ArgLysLysArgAsp just preceding the A chain in pTR411 are changed to codons for SerGluAlaAlaAsp in pTR601. In addition, the Asp codons at positions 99, 120, and 132 have been changed to Glu codons. The construction of pTR601 required four steps, detailed below, resulting in the intermediate plasmids pTR540-2, pTR550-8, and pTR561.

Figure 10:
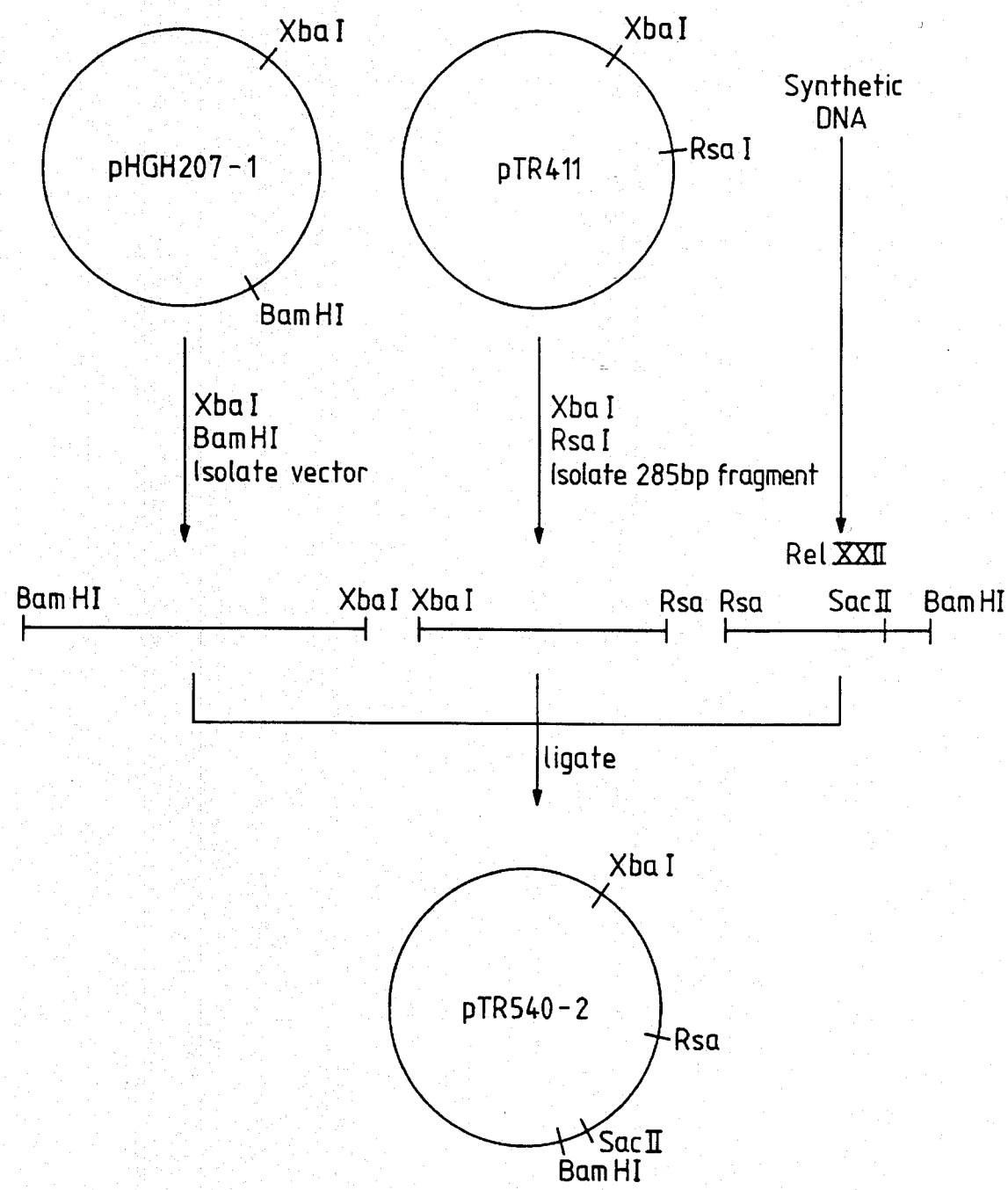
FIG. 10 illustrates diagrammatically the construction of plasmid pTR540-2.

Preparation of pTR540-2 (FIG. 10)

The plasmid pTR540-2 was constructed from three DNA fragments, the first of which was the vector pHGH207-1 (U.S. Pat. No. 4,663,283) in which the small XbaI-BamHI fragment had been removed. The second was a 285-bp XbaI-RsaI fragment isolated from pTR411 encoding the first 94 amino acids of Asp-inserted prorelaxin. The third was the 76-bp synthetic DNA duplex RelXXII of the sequence:

```
5
ACCTGTATTAAAAGAATCCAGTCTTCTCTTTGAAGAATTTAAGAAACTTATTCGCAATAGACAAG-
TGAA-3'-TGGACATAATTTTCTTAGGTCAGAAGAGAAACTTCTTAAATTCTTTGAATTCTTTGAATAA-
GCCGCG-3'
CGGCGCTAG-5'
```

The three fragments were ligated together using T4 ligase and used to transform E. coli cells. Transformants were selected on ampicillin plates and the plasmid pTR540-2 was selected by restriction analysis and DNA sequencing. The scheme for its preparation is shown in FIG. 10.

Figure 11:
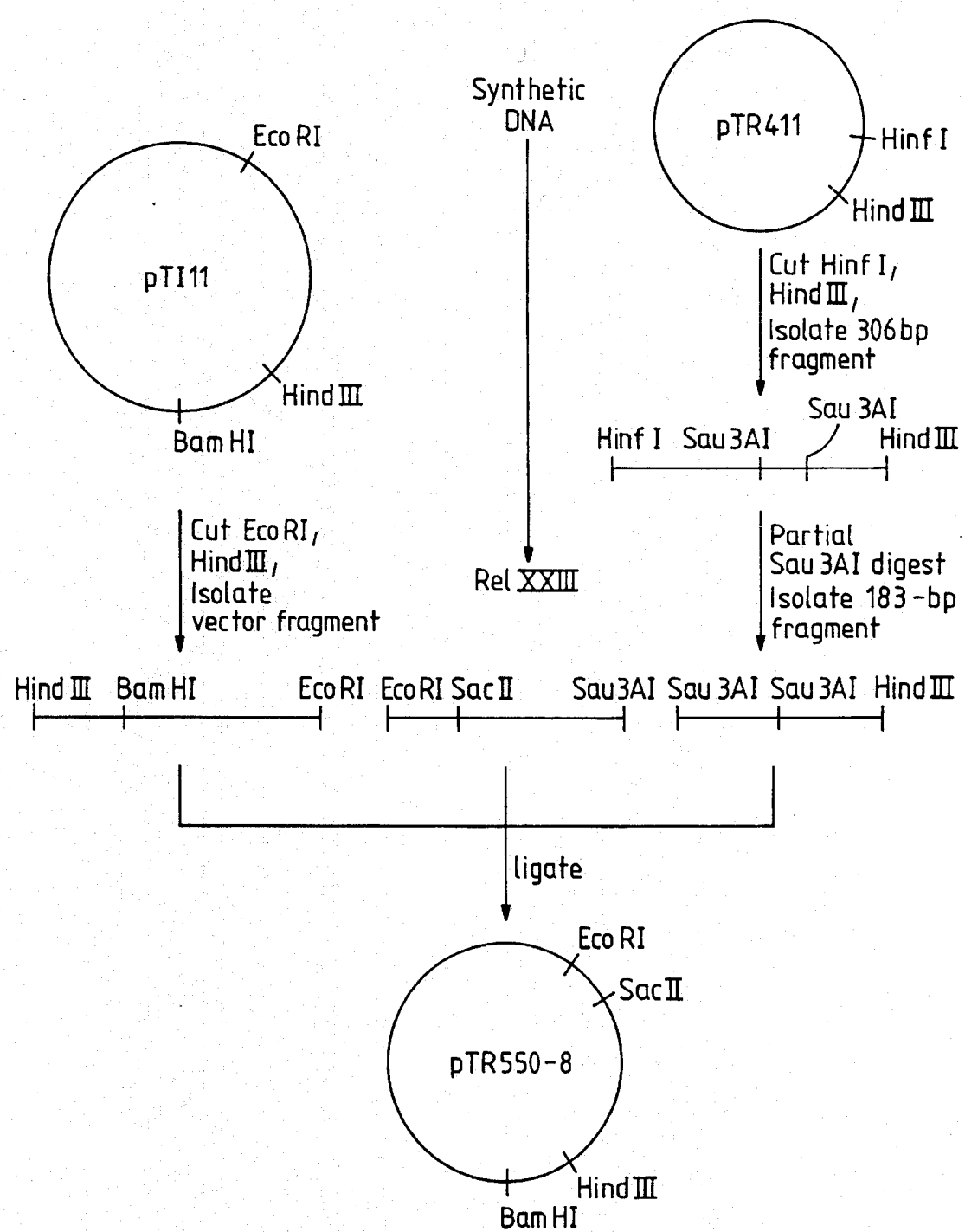
FIG. 11 illustrates diagrammatically the construction of plasmid pTR550-8.

Preparation of pTR550-8 (FIG. 11)

The plasmid pTR550-8 was prepared from three DNA fragments, the first of which was isolated from the cloning vector pTIll containing available EcoRI and HindIII restriction sites and treated with EcoRI and HindIII. The vector pTIll is a derivative of pHGH207-1 in which the human growth hormone-encoding sequence has been replaced by that for human interleukin-1. An alternative vector for this construction is the vector fragment isolated from pBR322 digested with EcoRI and HindIII.

The second fragment was the 65-bp synthetic duplex RelXXIII of the sequence:

The third part was the 183-bp Sau3AI-HindIII fragment from pTR411 encoding amino acids 140–164 of Asp-inserted prorelaxin. This last fragment was obtained by first isolating the 306-bp HinFI-HindIII fragment from pTR411 and then partially digesting this fragment with Sau3AI.

The three fragments were ligated together and the mixture was used to transform E. coli strain 294. Transformants were selected for ampicillin resistance and the plasmid pTR550-8 was selected by restriction analysis and DNA sequencing. The scheme for preparing TR550-8 is shown in FIG. 11.

Figure 12:
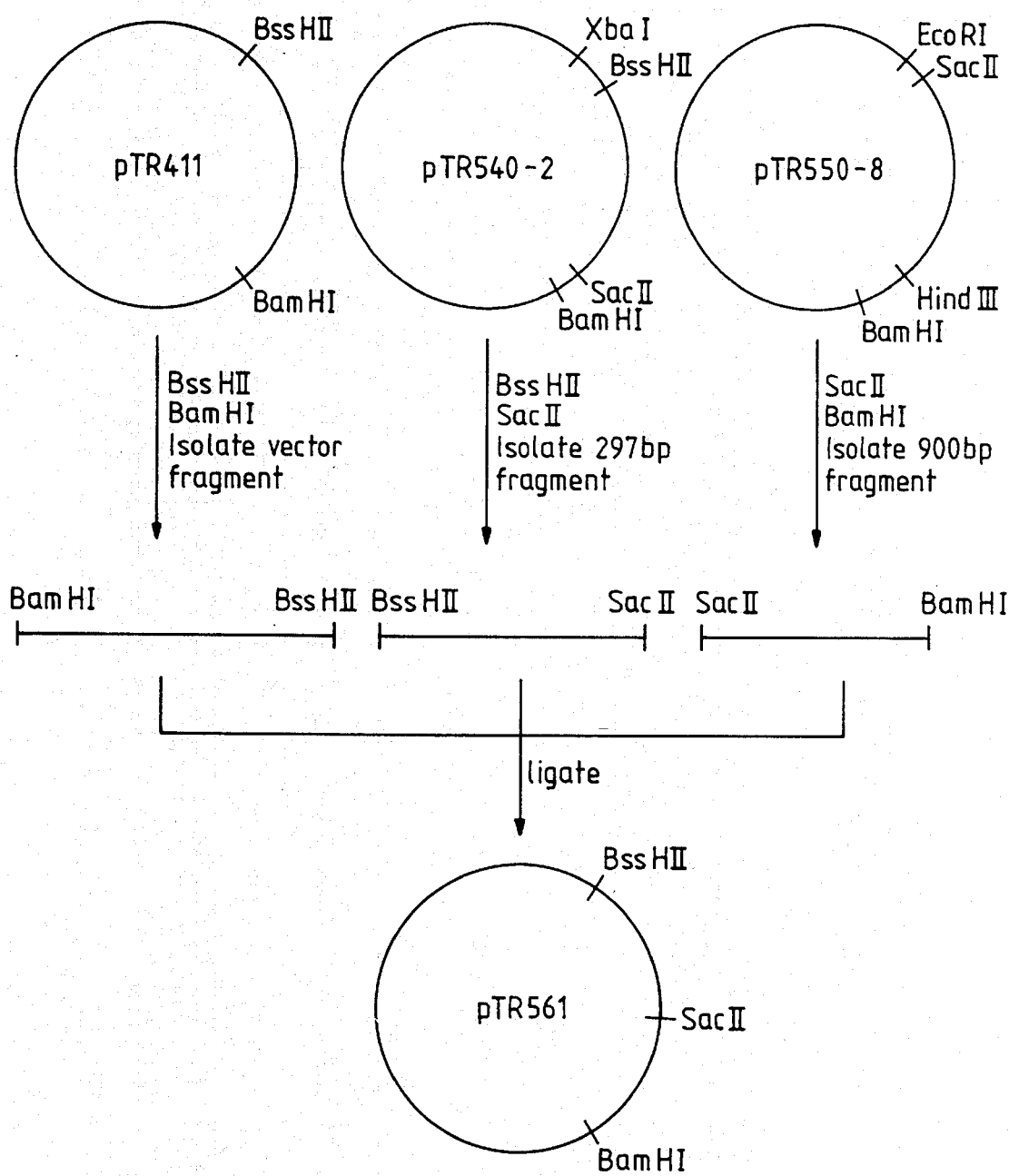
FIG. 12 illustrates diagrammatically the construction of plasmid pTR561 from fragments of pTR540-2 and pTR550-8.

Preparation of pTR561 (FIG. 12)

The plasmid pTR561 combines all of the coding sequence for Asp-inserted prorelaxin with the enhanced acid cleavage site. Three DNA fragments were used in the construction, the first of which was the vector pTR411 in which the small BssHII-BamHI fragment had been removed. The second was the 297-bp BssHII-SacII fragment obtained from pTR540-2. The third was the 900-bp SacII-BamHI fragment obtained from pTR550-8 encoding the last 45 amino acids of the enhanced Asp-inserted prorelaxin. This last fragment also contains some interleukin-1 sequence between the HindIII and BamHI sites that is not important for the construction.

The three fragments were ligated together with T4 ligase and used to transform E. coli strain 294 cells. Transformants were selected for ampicillin resistance and the plasmid pTR561 was selected by restriction analysis. The scheme for construction of pTR561 is shown in FIG. 12.

Figure 13:
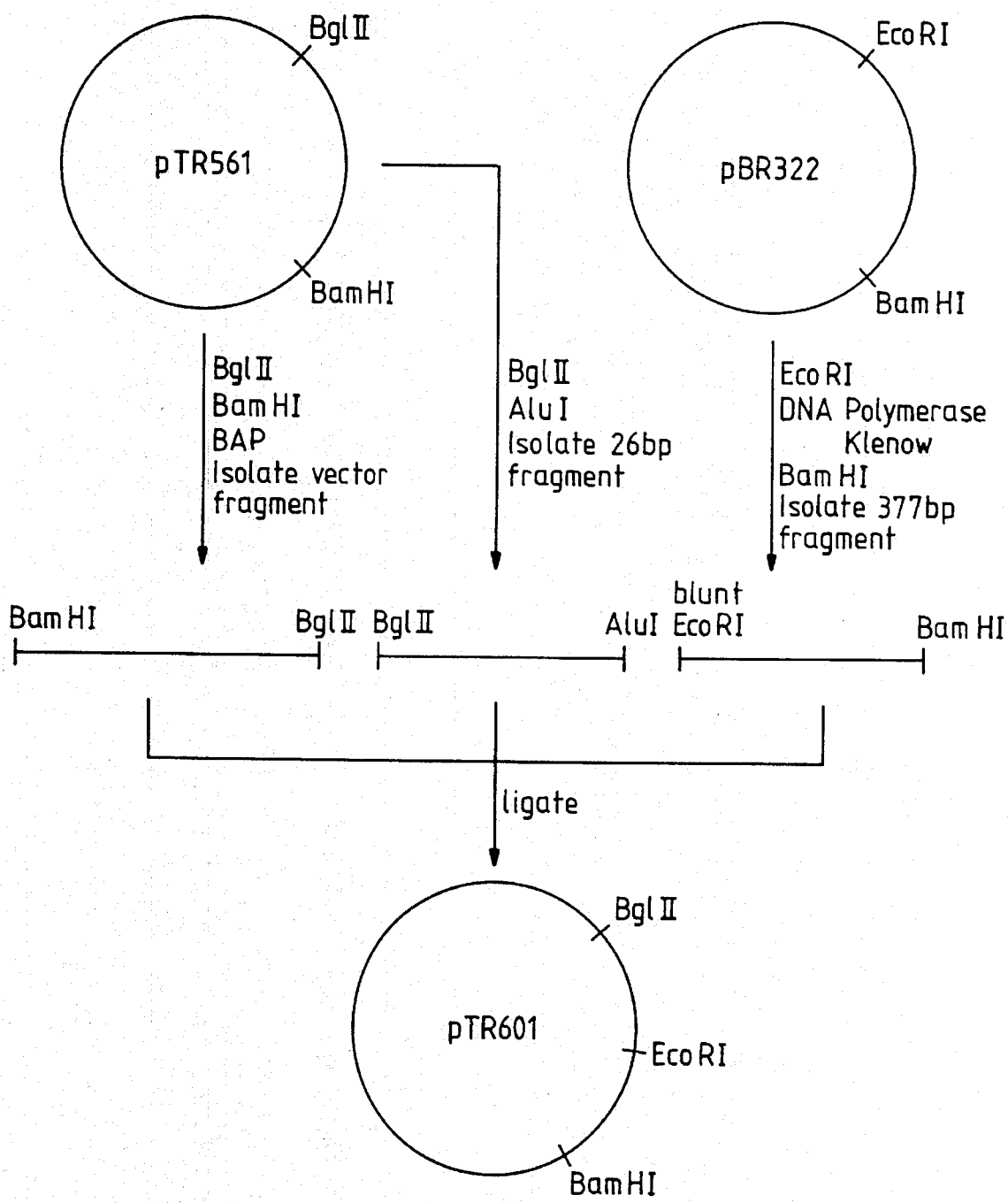
FIG. 13 illustrates diagrammatically the construction of plasmid pTR601 from fragments of pTR561 and pBR322.

Preparation of pTR601 (FIG. 13)

The final plasmid pTR601 removes all nonessential interleukin-1 sequence from pTR561 and restores the tetracycline resistance gene. Three fragments were used to construct pTR601, the first of which was the vector pTR561 in which the small BglII-BamHI fragment had been removed. This vector was then treated with bacterial alkaline phosphatase to prevent its recircularization. The second was a 26-bp BglII-AluI fragment obtained from pTR561 and encoding the last six amino acids of prorelaxin. The third was the 377-bp EcoRI-BamHI fragment from pBR322 in which the EcoRI site had been filled in with DNA polymerase Klenow.

The three fragments were ligated together and used to transform E. coli 294 cells. Transformants were selected for tetracycline resistance and the plasmid pTR601 was selected by restriction analysis. The scheme for the construction of pTR601 is shown in FIG. 13.

EXAMPLE 3

Expression of Gene Encoding, and Cleavage of, Asp-Inserted Human Prorelaxin With Enhanced Acid Cleavage Site The plasmid pTR601 described in Example 2 was used to transform the host cell W3110tonA using the protocol described below. E. coli W3110tonA host is a strain that is essentially resistant to T1 phage and constructed using standard laboratory techniques involving transductions with phage derived from P1 (see, e.g., J. Miller, *Experiments in Molecular Genetics*, Cold Spring Harbor Press: New York, 1972). This host was generally obtained as described in EP 183,469 published Jun. 4, 1986.

Approximately 25 ml of LB broth was inoculated with a single colony of W3110tonA host cells. This mixture was incubated until an $A_{550}$ of approximately 1.0 was obtained. This incubation mixture was then transferred to a chilled contrifuge tube and placed on ice for about 5 to 10 minutes, then centrifuged at 600 rpm for 5 minutes. The pellet was then resuspended in 8.0 ml. of ice cold 0.1M $CaCl_2$, vortexed, and allowed to sit on ice for 4 hours. After this time, the mixture was centrifuged at 6,000 rpm for 5 min., and the pellet resuspended in 1.0 ml. of 0.1M $CaCl_2$ in 15% glycerol. The suspension was allowed to sit on ice overnight.

For transformation, approximately 0.25 to 0.5 ng of pTR601 plasmid DNA was added to 50 μl of $CaCl_2$-treated competent cells and the mixture allowed to sit on ice for 1 hour. After heat shocking at 42° C. for 90 seconds, the mixture was transferred to ice for one minute after which 0.1 ml of LB broth was added. After a 1-hour incubation period at 37° C. the mixture was plated on LB agar plates containing 20 μg of tetracycline/ml. Frozen stock cultures were made from single colony in LB medium with 5 μg tetracycline/ml that had been grown to an $A_{550}$ of about 1.0 at 37° C. Cultures were frozen in 10% DMSO at −70° C.

For culture of the transformed cells, 500 ml of LB broth was inoculated with 0.5 ml of the frozen stock culture and incubated at 37° C. and 200 rpm for 8 hours. The seed culture thus obtained was placed in a 10-liter fermenter to which Trp 8 salts were added. Trp 8 salts consist of 5.0 g/L of ammonium sulfate, 6.0 g/L of $K_2HPO_4$, 3.0 g/L of $NaH_2PO_4$, and 1 g/L of sodium citrate.$2H_2O$. The Trp 8 salts (10 L) were sterilized in the fermenter in 7 liters of distilled water. After the fermenter had cooled, the following ingredients were added: 500 ml of 50% glucose, 100 ml of 1M $MgSO_4$, 5 ml of trace metals with iron, 5 ml of 2.7% $FeCl_3$, 250 ml of 20% Hycase, 250 ml of 20% yeast extract, and 10 ml of 5 mg/ml tetracycline.

The culture was grown at 37° C., pH 7.0, with aeration at 10 lpm, agitation at 1000 rpm, and back pressure at 0.3 bar. A slow feed of glucose was initiated at about $OD550_{nm}$ of 20. A total of 25 ml of a 25 mg/ml solution of 3-indole acrylic acid (IAA) was added at $OD550_{nm}$ of 30. The culture was harvested 8 hours after the addition of IAA. The cell pellet was collected via Sorvall R3CB and frozen at −20° C.

The Asp-inserted mutant human prorelaxin from pTR601 was purified from the cell paste as follows:

Cell paste from pTR601-transformed cells was processed by suspending it in lysis buffer (20 mM TrisHCl pH 8, 500 mM NaCl, 10 mM EDTA) in a 1:10 ratio. The suspension was passed through a Manton-Gaulin homogenizer at about 6,000 psi, three times. After centrifugation at 6000 xg for 30 minutes, the pellet was solubilized into 4M guanidine-HCl/ 20 mM Tris-HCl pH 8/0.1% β-mercaptoethanol (BME). This solution was ultrafiltered and diafiltered into 20 mM $NH_4$ acetate buffer, pH 4.5, 6M urea/0.1% BME. This material was loaded into a sulfopropyl-trisacryl (SPTA) column (LKB Produkter).

SPTA fractionation was undertaken in order to achieve an initial purification of the mutant Asp-inserted prorelaxin. The column dimensions were about 10×12 cm, which correspond to about a 950 ml bed volume. The buffer employed was 25 mM $NH_4$ acetate/6M urea/0.1% BME. The flow rate employed was about 30 ml/min, which was equal to about 1.8 liters per hour. A 5 column volume gradient of 0–0.65M NaCl in column buffer was employed. In a typical fractionation run, approximately 1 kilogram of cell paste was fractionated for every 2.5 liters of resin.

SDS-polyacrylamide gel electrophoresis (15%) was performed on various fractions to determine pooling parameters. Pools containing the mutant Asp-inserted human prorelaxin protein were ultrafiltered/diafiltered into 4M guanidine-Cl/20 mM Tris-HCl, pH 8.0/0.1% BME and loaded onto a Sephacryl-300 column in the same buffer.

The Sephacryl-300 column employed had dimensions of 5.0×90 cm (a 1.7 liter bed volume), with a flow rate of about 100 ml/hr. Generally, a ratio of resin/paste of 14 L/kg paste was employed. Again, SDS polyacrylamide gel electrophoresis was performed on column fractions to determine pooling parameters. The pools containing essentially purified mutant Asp-inserted Met-prorelaxin were collected and diafiltered using 4 volumes of 7.5M urea and 0.1% BME and then diafiltered using 20 volumes of 0.5N acetic acid. The second diafiltration step was conducted in the absence of oxygen by purging the reaction vessel with helium gas to maintain the prorelaxin in a reduced form.

Enhanced acid cleavage was performed under the following conditions: a protein concentration of about 1 mg/ml and incubation at 110° C. for 4 hours without evacuation of the reaction vessel. Then the hydrolysate was dried down in a rotary evaporator and dissolved in buffer with 4M urea, 20 mM Tris, and 100 mM DTT, pH8 and the solution was loaded on a S-Sepharose Fast Flow column equilibrated in the same buffer. The A chain adhered to the column and a gradient of sodium chloride was used to elute the A chain. The A chain pool was exchanged into 0.5N acetic acid on a G25 gel filtration resin and dried in a rotary evaporator. Then the A chain was dissolved in 4M guanidine-Cl, 20 mM Tris HCl, pH 8, and 100 mM DTT. Finally, the samples were purified preparatively by HPLC as described below.

HPLC was performed on a Vydac C-4 reverse phase column under the following conditions:

Vydac C-4 RPC (4.6×250 mm, 300A, 5μ)

0.1% TFA/water 0.1% TFA/acetonitrile

15–55% gradient 0.5% per minute, 2 ml per minute 280 nm-AUFS 0.02; 214 nm-AUFS 0.1

0.2 cm per minute chart speed

As will be appreciated, three main peaks were obtained, designated peaks 1, 2, and 3, respectively. Fractions corresponding to peaks 1, 2, and 3 were collected and sequenced and amino acid compositions determined. The peptide from peak 1 was found to contain sequences corresponding to cleavage fragments from the C peptide region of prorelaxin. The peptide from peak 2 was found to have no apparent sequence, because the N-terminal glutamine had cyclized to the pyro-glutamic acid form, which does not respond to Edman degradation. The peak 2 peptide was determined to be A chain upon amino acid composition analysis and mass spectrometry. The peptide from peak 3 was found to correspond to des($Asp_1$)-B chain.

The approximate elution position of the three peptides was as follows: pyroGlu A chain (peptide 2) eluted at an apparent acetonitrile concentration of about 26.0% and des($Asp_1$) B chain eluted at an apparent acetonitrile concentration of about 43.6%.

The approximate recovery of A chain peptide, based on the mass of A chain, relative to the amount present in the starting Met-Asp-inserted prorelaxin in the acetic acid cleavage protocol, was found to be about 38–42%. The identical experiment without the helium purge during the second diafiltration step resulted in a yield of 27%.

Samples containing the column-purified A chain material were stored at –20° C. until used.

Comparative experiments using pTR411 as the expression vector were performed repeating the above protocol except that the cleavage was performed as follows:

Freshly purified samples from the Sephacryl-300 column were dialyzed overnight against about 100 volumes of 0.5M acetic acid. Cleavage was performed under the following conditions: a protein concentration in the range of about 0.25 to 2.0 mg/ml was typically employed. The samples were incubated at 110° C. for 18 hrs., and evacuated to final conditions of approximately 2 torr. Samples were then stored at –20° C. until analyzed or preparatively collected by HPLC.

Under the above conditions, the approximate recovery of A chain peptide obtained, based on the mass of A chain relative to the amount present in the starting Met-Asp-inserted prorelaxin in the acetic acid cleavage protocol, was originally thought to be approximately 40–50% for the pGlu-A-chain. When the experiment was repeated several times and the products were analyzed more fully by HPLC and mass spectroscopy, it was found that what was thought to be the A chain was an extended A chain and that the recovery of A chain was between approximately 5 and 10%. When the experiment was repeated by alternate purge cycles of helium gas followed by evacuation, the yields of relaxin A chain did not significantly improve.

It was found that the yield of A chain from the enhanced Asp cleavage prorelaxin (from pTR601) varied dramatically depending on several parameters described below.

The optimal cleavage time for 0.5N acetic acid at 110° C. was found to be about 2 to 10 hours, most optimally about 4–8 hours.

When the enhanced acid cleavage experiment was repeated using relaxin A prepared by the Merrifield peptide synthesis rather than recombinant relaxin A, about 50% of the recoverable protein was degraded. Some of the primary sites of hydrolysis appeared to be cysteine residues, and, to a lesser degree, serine residues.

When the enhanced acid cleavage experiment was repeated except that 0.001–0.003N trifluoroacetic acid, 0.005N sulfuric acid, or 0.03–0.05N hydrochloric acid was employed, it was found that of all the acids tested, 5 mM sulfuric acid and 0.5N acetic acid gave the best yields.

When the enhanced acid cleavage experiment was repeated except that prorelaxin concentration was increased from 1 mg/ml to 19 mg/ml, it was found that the HPLC C4 peak for A chain decreased from about 9 cm at about 1 mg/ml to 6.4 cm at 8 mg/ml to 5.6 cm at about 19 mg/ml.

When the enhanced acid cleavage experiment was repeated except that 1–10 mM dithiothreitol (DTT) was used instead of BME in the first diafiltration step, the yield of A chain decreased substantially.

When the enhanced acid cleavage experiment was repeated except that 1 and 10 mM oxidized cysteine (cystine) was added to the acetic acid hydrolysis mixture, the yield of A chain decreased markedly.

When the enhanced acid cleavage experiment was repeated except that after the first dialysis, the samples of prorelaxin were allowed to stand in the urea/BME dialysis buffer for periods greater than three days before being dialyzed using the acetic acid, the yield of A chain was reduced to 24–25%. A suitable time to initiate cleavage after reducing conditions are imposed would be 0 to 2 days, preferably 0–24 hours, most preferably immediately. These experiments suggest that the formation of disulfide bonds in the molecule should be avoided to obtain maximum yields from the hydrolysis reaction. Further, these results show that, unexpectedly, disulfide bonds can be formed under acid conditions, which are not conducive therefor.

The sample containing the HPLC-purified A chain can be used to reconstitute relaxin as described in Example 4.

EXAMPLE 4

Reconstitution of Relaxin Employing Relaxin Peptides

The following protocol(s) can be employed in order to reconstitute relaxin using purified A chain obtained as above.

Method I:

Refolding is performed in a total volume of about 1142.5 µl, composed as follows: 100 µl of 0.5M glycine (BioRad Laboratories), pH 10.5, 100 82 1 6M urea (Mallinckrodt), 725 µl water, 50 µl acetonitrile (Burdick and Jackson), 15 µl 1-propanol (Burdick and Jackson), 100 µl of A chain solution (3 mg/ml relaxin A chain in water) and 62.5 µl of B chain solution (504 µg relaxin B chain in 350 µl 6M urea). The samples are refolded overnight at 20° C. with gentle mixing.

Method II

Refolding is performed in a mixture composed as follows: 0.2–1M CAPS buffer (3-[cyclohexylamino]propanesulfonic acid, CalBioChem), pH 10.2, 0.75M guanidine hydrochloride, 10% (v/v) methanol (Burdick and Jackson), and a range of total protein concentration from 0.25 to 2.0 mg/ml. The protein ratio of relaxin A chain to relaxin B chain should be on the order of about 4 parts A chain and 1 part B chain. The solution should be thoroughly purged with an inert gas such as $N_2$ or argon and stirred overnight in the presence of air (12–18 hrs.) at 20° C.

All folded samples may be assayed for activity and/or repurified by HPLC essentially as previously described (Example 3).

Large-scale refolding is obtained by increasing the overall amounts of materials proportionally.

EXAMPLE 5

Construction and Expression of Genes Encoding, and Cleavage of, Asp-Inserted Polymeric A Chain Human Prorelaxin Mutants The generation of polymeric forms of A-chain to improve expression using acetic acid cleavage to hydrolyze the polymer was investigated in this example.

Four plasmids were constructed that had three or four relaxin A chains together that were linked with the sequence:

-Glu-Ala-Ala-Asp-RlxA-[Asp-Pro-Ser-Ala-Asp-RlxA]$_{2-3}$, or

Figure 14:
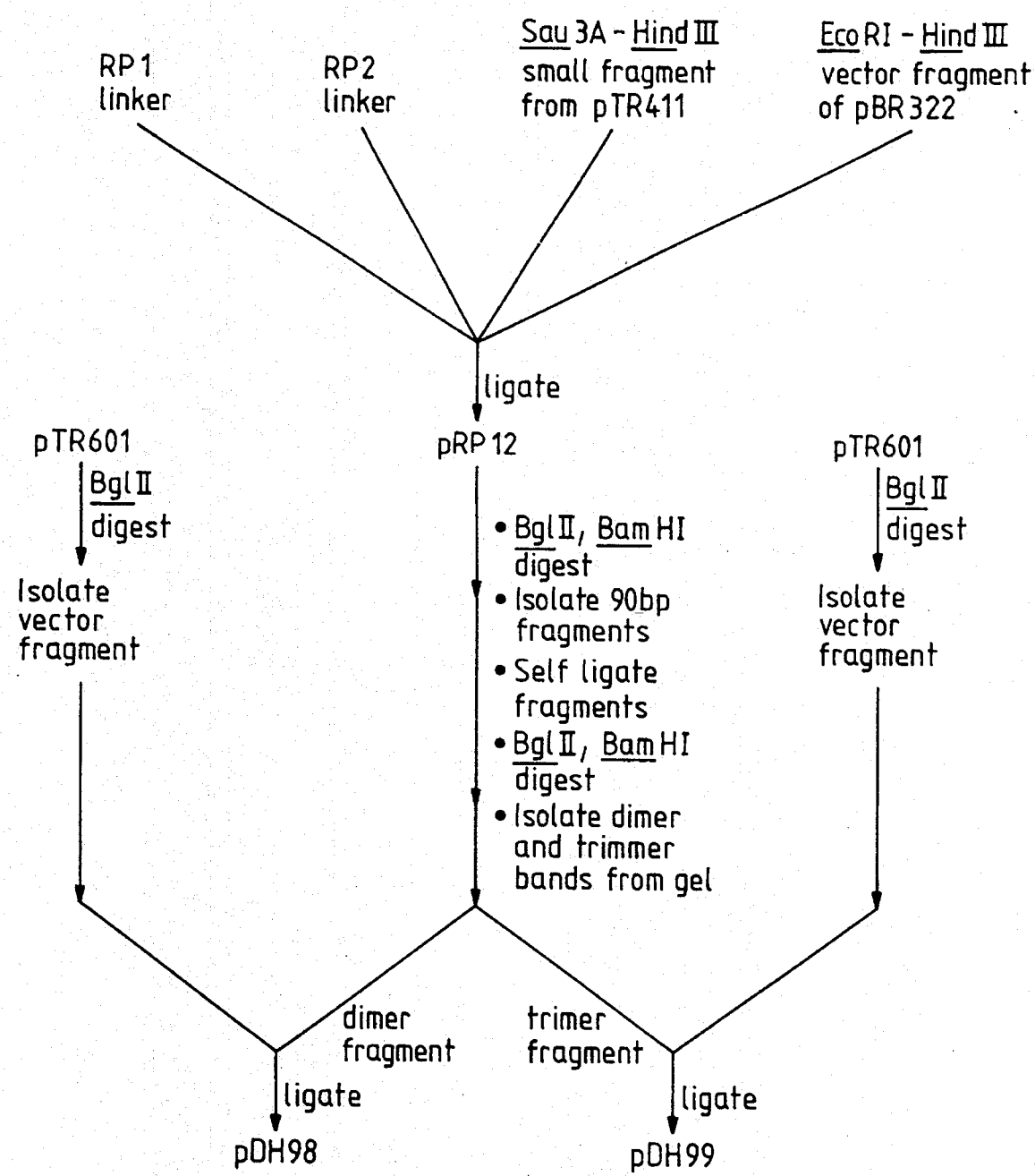
FIG. 14 illustrates diagrammatically the construction of plasmids pDH98 and pDH99.
Figure 15:
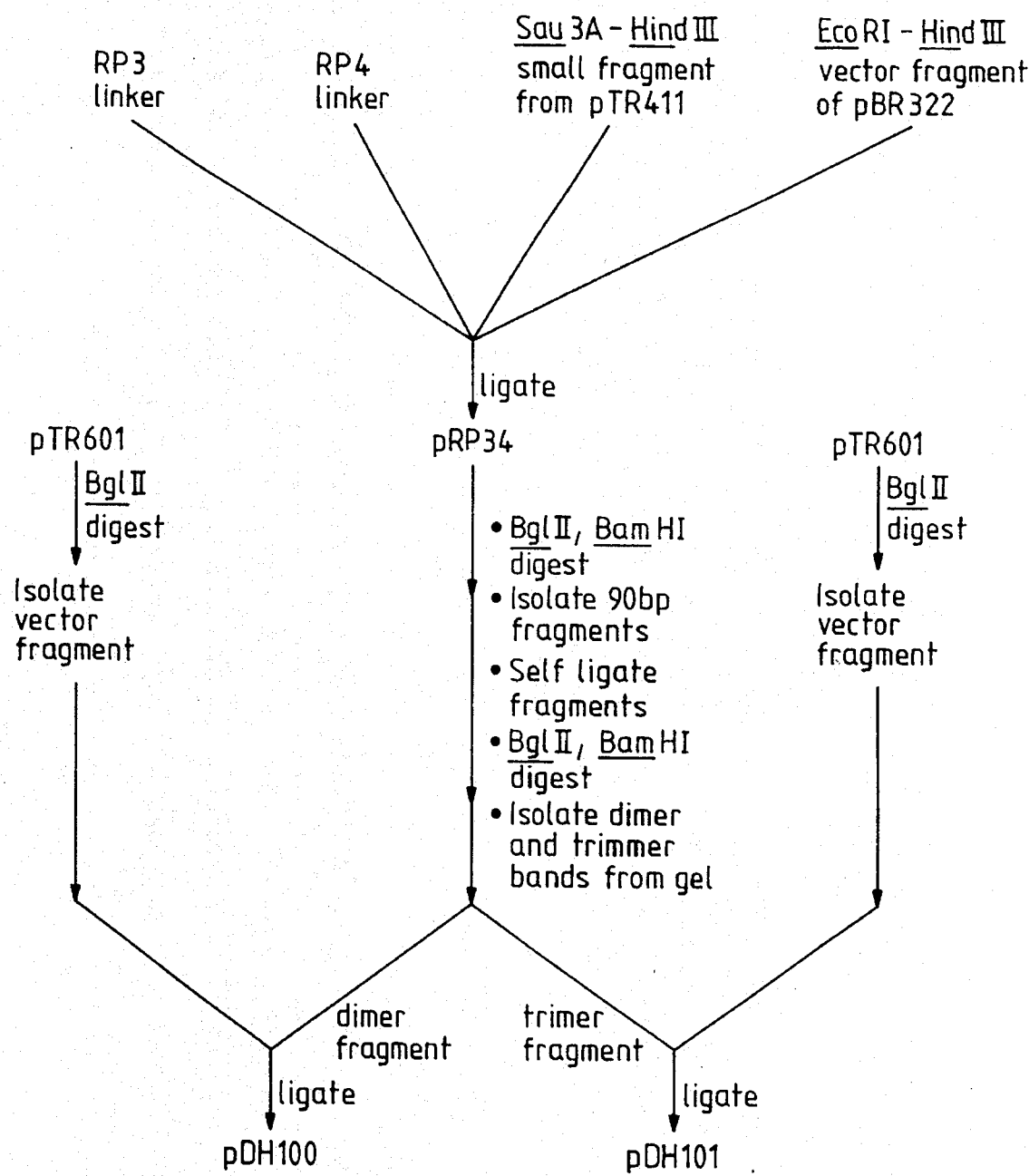
FIG. 15 illustrates diagrammatically the construction of plasmids pDH100 and pDH101.

-Glu-Ala-Ala-Asp-RlxA-[Asp-Gly-Ser-Ala-Asp-RlxA]$_{2-3}$, where RlxA is relaxin A chain. The constructions of these plasmids are detailed below and in FIGS. 14 and 15, respectively. Two intermediate plasmids pRP12 and pRP34 linking the back end of the A chain through the appropriate linker to the front end of the A chain were prepared as follows: Synthetic oligonucleotide linkers of the following sequence were prepared by phosphoramide synthesis:

```
RP1 5'-AATTGGATCCCTTGCTAGATTTTGCGATCCTTCAGCA-3'
RP2 3'-       CCTAGGGAACGATCTAAAACGCTAGGAAGTCGTCTAG-5'

RP3 5'-AATTGGATCCCTTGCTAGATTTTGCGATGGTTCAGCA-3'
RP4 3'-       CCTAGGGAACGATCTAAAACGCTACCAAGTCGTCTAG-5'

<——— C terminus of A ———><——— linker ———>
```

The next piece was a partial Sau3A-HindIII fragment from pTR411 (FIG. 9) that contains the entire relaxin A chain and places the last Asp of the linkers shown above in front of the first amino acid of relaxin.

Fragment from pTR411:

```
5'-GATCAACTCT ACAGTGCATT GGCTAATAAA TGTTGCCATG TTGGTTGTAC
CAAAAGATCT
3'-           TTGAGA TGTCACGTAA CCGATTATTT ACAACGGTAC AACCAACATG
GTTTTTCTAGA
        GlnLeuT yrSerAlaLe uAlaAsnLys CysCysHisV alGlyCysTh
rLysArgSer

CTTGCTAGAT TTTGCTGAGA TGAAGCTAAT TGTGCACATC TCGTATAATA TTCACACATA
GAACGATCTA AAACGACTCT ACTTCGATTA ACACGTGTAG AGCATATTAT AAGTGTGTAT
LeuAlaArgP     heCysOP*

TTCTTAATGA CATTTCACTG ATGCTTCTAT CAGGTAATTC TCATGTTTGA CAGCTTATCA
AAGAATTACT GTAAAGTGAC TACGAAGATA GTCCATTAAG AGTACAAACT GTCGAATAGT

TCGATA-3'
AGCTATTCGA-5'
```

Two ligations were employed using T4 ligase and the components:

pRP12: RP1 plus RP2 plus pTR411 fragment plus EcoRI-HindIII vector fragment of pBR322, and pRP34: RP3 plus RP4 plus pTR411 fragment plus EcoRI-HindIII vector fragment of pBR322.

Strain MM294tonA (prepared by a standard transduction method generally as described in EP 183,469 published Jun. 4, 1986) was transformed with each of the above plasmids using a standard *E. coli* transformation protocol. Miniscreen restriction analysis and sequencing were done to confirm that the correct sequence was obtained. From each of these plasmids a BglII-BamHI digestion will release a fragment that contains the back end of the A chain, the appropriate linker fragment, and the front end of the A chain.

The expression plasmid pTR601 was digested with BglII, which cuts once in the plasmid in the A chain coding region, and then treated with bacterial alkaline phosphatase to reduce religation of the vector.

Both pRP12 and pRP34 were individually digested with BglII and BamHI and the approximately 90-bp fragments were isolated from acrylamide gels. These fragments were self-ligated to form polymers, which could go together in a variety of ways, represented below:

```
digestion                                  → → → ← →
→ ← ← → → ←                                 
with   BglII                               
 -  +  -  +  -  +                            -  -  +  +
and    BamHI      trimer mon.dimer dimer   dimer   monomer
``` where mon. is monomer and → is Bam to Bgl and ← is Bgl to Bam.

Subsequent digestion with BglII and BamHI should only leave head to tail polymers, as those junctions are resistant to cleavage with both enzymes. After this digestion, the DNA was run on an acrylamide gel and the dimer bands of approximately 180 and the trimer bands of approximately 270 were eluted from the gel, separately for the pRP12 and pRP34 fragments. These DNA fragments were ligated into the pTR601 vector fragment described above and the resulting ligated construct was transformed into strain MM294tonA as described above. Transformants were analyzed by miniscreen restriction analysis for the correct plasmids. Four plasmids were isolated as outlined below:

| Name | A chains | FIG. | No. of Linker |
|---|---|---|---|
| pDH98 | 3 | 14 | AspProSerAlaAsp |
| pDH99 | 4 | 14 | AspProSerAlaAsp |
| pDH100 | 3 | 15 | AspGlySerAlaAsp |
| pDH101 | 4 | 15 | AspGlySerAlaAsp |

Each of these plasmids were used to transform W3110tonA cells and the resulting cell cultures were grown up using the conditions described above for pTR601-transformed cells. Each expressed a protein of the expected molecular weight. The *E. coli* fermenter pastes were stored at −80° C.

1 g cell paste from the fermenter was suspended in 10 volumes of ice-cold cell suspension buffer (25 mM Tris HCl, 5 mM EDTA, 10 mM DTT pH 7.5 at 25° C.) and sonicated for 5 min. using an Ultrasonics sonicator with Microtip probe at power setting 6 and 40% duty cycle, with cooling by immersion in an ice/ethanol bath. After centrifugation at 12,000 × g for 10 min. at 4° C., the pellet was resuspended in a similar volume of 7M urea, 25 mM Tris HCl, 5 mM EDTA, 10 mM DTT pH 7.5 at 25° C. and sonicated as before. After centrifugation at 27,000 × g for 20 min. at 4° C., the supernatant was decanted and filtered through a 0.45 micron Millex HA filter. The density of the supernatant was increased by addition of glycerol to 10% v/v and the sample was chromatographed on a Sephacryl S200 column (5×80 cm) equilibrated in 6M urea, 1M NaCl, 25 mM Tris HCl, 5 mM EDTA, 10 mM DTT, pH 7.5. The column was developed at 4° C. in the equilibration buffer at a flow rate of 1.5 ml/min. Fractions were pooled based on SDS polyacrylamide gradient gel (8–25%) detection of protein, and were stored at 4° C. until the hydrolysis step. Identity was confirmed by N-terminal sequence analysis.

As required, samples were taken from the S200 elution pool and dialyzed overnight at 4° C. in 8 Kd molecular weight dialysis tubing (Spectrapor) against 1000 volumes of 0.5N acetic acid. A protein concentration of 1.0 mg/ml was typically employed. Cleavage was performed by sealing the sample in an air-tight container and incubating it at 110° C. for 6 hours. Samples were then diluted and analyzed by high performance liquid chromatography, as described previously, using the following conditions.

SynChropak C-4 RPC (4.6×100 mm, 300A)

0.1% TFA/water 0.08% TFA/acetonitrile

15–55% gradient 1.0% per minute, 1 ml per minute 280 nm-AUFS 0.02; 214 nm-AUFS 0.2

2 mm per minute chart speed

The peak coeluting with authentic standard synthetic A chain on the HPLC column was shown by mass spectrometry to be pyroglutamic A chain.

The approximate recoveries of A chain peptide, normalized to a starting quantity of 1 g of fusion protein, after hydrolysis, were:

| | |
|---|---|
| pDH98 (D-P 3-mer) | 87 mg |
| pDH99 (D-P 4-mer) | 145 mg |
| pDH101 (D-G 4-mer) | 55 mg |
| Asp-Prorelaxin | 55 mg |

Thus, the A chain recovery from the D-P fusion proteins was about 36% of theoretical, which is 1.6 to 2.6 fold greater than from the Asp-inserted prorelaxin, depending on the number of A chain monomers in the fusion proteins.

The choice of how many A chains to put on the plasmid was governed by the fact that the polymer with four A chains was the largest ligation polymer recovered. How to synthesize larger polymers would be evident to any one of skill in the art.

The foregoing description of the invention has been directed to particular preferred embodiments in accordance with the requirements of the Patent Statutes and for the purposes of explanation and illustration. It will be apparent, however, to those skilled in the art that many modifications and changes in the techniques disclosed herein may be made without departing from the scope and the spirit of the invention. For example, there are numerous methods available to those skilled in the art for obtaining specific mutations in DNA sequences. Moreover, there are numerous methods known for obtaining host cell expression and isolation of recombinant products. Those of skill in the art will recognize that many alterations and changes may be made in the particular methods employed herein and nevertheless similar results are obtainable. These and all other modifications of the invention are intended to be included within the scope of the present invention as defined by the appended claims.

What is claimed is:

1. A process for preparing human, monkey, shark, pig, rat or mouse relaxin A chain comprising:

(a) culturing prokaryotic cells containing a first DNA sequence encoding relaxin C chain and A chain and a second DNA sequence encoding a linking chain consisting of Ser-Glu-Ala-Ala-Asp, wherein the second DNA sequence is located at the junction within the first DNA sequence encoding the relaxin C chain and A chain, thereby forming an Asp-A chain junction, said culturing resulting in the expression of a relaxin C chain-linking chain-relaxin A chain polypeptide in said prokaryotic cells;

(b) recovering said polypeptide;

(c) placing said polypeptide under reducing conditions so as to form a reduced free-cysteine form of said polypeptide; and (d) treating said reduced free-cysteine form of said polypeptide with an acid at a pH of about 1 to about 3 under conditions for cleaving the polypeptide at the Asp-A chain junction.

2. The process of claim 1 wherein the recovered polypeptide is maintained under a non-oxidizing atmosphere prior to step (d).

3. The process of claim 2 wherein the non-oxidizing atmosphere is an inert gas or nitrogen atmosphere.

4. The process of claim 1 wherein before step (a) the cells are transformed with an expression vector comprising said first DNA.

5. The process of claim 4 wherein the cells are *E. coli*.

6. The process of claim 5 wherein said expression vector is a plasmid.

7. The process of claim 1 additionally comprising the step of separating and isolating said relaxin A chain after step (d).

8. The process of claim 7 additionally comprising combining the isolated relaxin A chain with a corresponding human, monkey, shark, pig, rat or mouse relaxin B chain.

9. The process of claim 8 wherein the relaxin A and B chains are H2 relaxin chains.

10. The process of claim 1 wherein the first DNA encoding the A-chain encodes an A-chain of H2 or H1 relaxin.

11. The process of claim 10 wherein the first DNA encodes H2 relaxin A-chain.

12. The process of claim 1 wherein the acid is acetic acid, hydrochloric acid, or sulfonic acid.

13. A process for producing biologically active H1 or H2 relaxin comprising the steps of:

(a) providing an expression vector comprising a first DNA whose sequence encodes a polypeptide comprising a human relaxin H1 or H2 A-chain as shown in FIG. 1, wherein an Asp codon is introduced into said first DNA sequence as part of a second DNA sequence encoding an amino acid sequence Ser-Glu-Ala-Ala-Asp to precede the codon of the first amino acid of the human relaxin A chain, thereby forming an Asp-A chain junction;

(b) transforming a procaryotic host cell with said expression vector;

(c) culturing the transformed cell so as to produce a polypeptide comprising the human relaxin A-chain;

(d) recovering the polypeptide from the culture;

(e) placing said polypeptide under reducing conditions so as to form a reduced, free-cysteine form of the recovered polypeptide;

(f) treating said reduced, free-cysteine form of the recovered polypeptide with acid at a pH of about 1 to about 3 under conditions for cleaving the polypeptide at the Asp-A chain junction to form cleavage products;

(g) separating the human relaxin A-chain from other cleavage products; and (h) combining the human relaxin A-chain with a corresponding H1 or H2 human relaxin B chain having the sequence of human relaxin B as shown in FIG. 1 to produce biologically active human relaxin.

14. The process of claim 13 wherein step (e) comprises dialyzing or diafiltering said polypeptide into a buffer comprising a reducing agent and which is maintained under a non-oxidizing atmosphere.

15. The process of claim 14 wherein the non-oxidizing atmosphere is an argon or helium atmosphere and step (f) comprises dialyzing or diafiltering the polypeptide into the acid solution from 0 to 24 hours after the first dialysis or diafiltration step and wherein the polypeptide is maintained in contact with acid for from 2 to 10 hours.

* * * * *